(12) United States Patent
Yoon et al.

(10) Patent No.: US 12,290,378 B2
(45) Date of Patent: May 6, 2025

(54) SMART PSEUDO-PALATE FOR LINGUISTIC AND BIOMEDICAL APPLICATIONS

(71) Applicant: University of Florida Research Foundation, Inc., Gainesville, FL (US)

(72) Inventors: Yong Kyu Yoon, Gainesville, FL (US); Ratree Wayland, Gainesville, FL (US); Lori J. Altmann, Gainesville, FL (US); Saeyeong Jeon, Gainesville, FL (US); Sunghyun Hwang, Gainesville, FL (US); Kevin Tang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 710 days.

(21) Appl. No.: 17/351,542

(22) Filed: Jun. 18, 2021

(65) Prior Publication Data

US 2021/0393193 A1    Dec. 23, 2021

Related U.S. Application Data

(60) Provisional application No. 63/042,749, filed on Jun. 23, 2020.

(51) Int. Cl.
*A61B 5/00* (2006.01)
*A61B 5/053* (2021.01)

(52) U.S. Cl.
CPC ............ *A61B 5/4803* (2013.01); *A61B 5/053* (2013.01); *A61B 5/4552* (2013.01); *A61B 5/682* (2013.01);
(Continued)

(58) Field of Classification Search
CPC ..... A61B 5/4803; A61B 5/053; A61B 5/4552; A61B 5/682; A61B 5/6843; A61B 2562/162; A61B 2562/166
See application file for complete search history.

(56) References Cited

U.S. PATENT DOCUMENTS 4,112,596 A * 9/1978 Fletcher ............... A61F 5/58
600/595
4,175,338 A * 11/1979 Takinishi ............ A61B 5/287
29/850

(Continued)

FOREIGN PATENT DOCUMENTS

DE      29906206 U1 *  9/1999  .......... A61B 5/0088
WO   WO-0010450 A1 *  3/2000  ............ A61B 5/228

*Primary Examiner* — Eun Hwa Kim
(74) *Attorney, Agent, or Firm* — Thomas|Horstemeyer, LLP

(57) ABSTRACT

In one aspect, the disclosure relates to a smart pseudo-palate for use in a Smart Electropalatograph (EPG) for Linguistic and Medical Applications (SELMA) system. In one aspect, the pseudo-palate is constructed from a thin, flexible polymer membrane and having an embedded electrode array. The pseudo-palate is configured to detect tongue contacts during speech while causing minimal disturbance or interference with speech motion. The disclosed pseudo-palate in the SELMA system is integrated with a microcontroller, wireless electronic module, and external readout app. The disclosure, in another aspect, relates to integration of the pseudo-palate with a smart sports/health mouth guard containing a series of sensors for monitoring head impacts, body temperature, and heart rate. The SELMA system is capable of automated detection of neurological conditions and brain injury including, but not limited to, concussion, and neurological movement disorders, using acoustic, articulatory, and other biosignals from the device using deep data analysis.

15 Claims, 12 Drawing Sheets

(11 of 12 Drawing Sheet(s) Filed in Color)

(52) U.S. Cl.
CPC .... *A61B 5/6843* (2013.01); *A61B 2562/0215* (2017.08)

(56) References Cited

U.S. PATENT DOCUMENTS

| | | | | |
|---|---|---|---|---|
| 4,287,895 | A * | 9/1981 | Hori | A61B 5/6852 600/595 |
| 5,212,476 | A * | 5/1993 | Maloney | A61B 5/394 455/100 |
| 2002/0087322 | A1* | 7/2002 | Fletcher | A61B 5/228 704/270 |
| 2013/0041235 | A1* | 2/2013 | Rogers | H05K 1/0283 600/386 |
| 2014/0303452 | A1* | 10/2014 | Ghaffari | H01L 27/14687 601/3 |
| 2015/0305671 | A1* | 10/2015 | Yoon | A61B 5/01 600/28 |
| 2017/0143960 | A1* | 5/2017 | Kent | A61B 5/4818 |
| 2019/0091061 | A1* | 3/2019 | Radmand | A61F 5/566 |

\* cited by examiner

SMART PSEUDO-PALATE FOR LINGUISTIC AND BIOMEDICAL APPLICATIONS

CROSS REFERENCE TO RELATED APPLICATIONS

This application claims the benefit of U.S. Provisional Application No. 63/042,749 filed on Jun. 23, 2020, which is incorporated herein by reference in its entirety.

STATEMENT REGARDING FEDERALLY SPONSORED RESEARCH OR DEVELOPMENT

This invention was made with government support under grant number 2037266 awarded by the National Science Foundation. The government has certain rights in the invention.

BACKGROUND

A growing body of research has suggested that speech has the potential to detect physical and mental health issues, such as concussions, Parkinson's disease (PD), schizophrenia, depression, fatigue and stress. While its use for diagnosing concussions is promising, the reported predictive power of speech is far from being reliable.

Traumatic brain injury (TBI) is a disruption of normal brain functions caused by head injuries such as a bump, blow, or jolt to the head. TBIs can result in adverse physical, cognitive and behavioral consequences, and even mild traumatic brain injuries (mTBI, also known as concussions) can cause extensive short and long-term adverse effects on cognition and neurologic function, and impair socioemotional health and academic achievement, particularly among children and young adults with immature brains. According to a study conducted by the American Academy of Neurology in 2000, six out of ten NFL athletes have suffered from concussions and nearly 300,000 cases of concussions are diagnosed in young athletes in the US each year. Unfortunately, nearly 90% of concussions remain undetected due to the subtlety of symptoms, a lack of reliable biomarkers that can quickly and non-intrusively detect signs of concussions, and a lack of portable objective diagnostic methods that can be administered shortly after a concussion event.

Existing classification models of speech after concussion only employ acoustic information to infer motor control issues in speech, while ignoring articulatory information which can provide a more direct and complementary estimate of the speed, strength, and accuracy of rapid motor speech movements. In addition, since recording often takes place in non-optimal conditions, certain acoustic features cannot be measured reliably due to excessive noise levels in the recording. Incorporating an additional articulatory dimension will likely improve the diagnostic model's accuracy. Electropalatography (EPG) measures physical contacts between the tongue and hard palate in the vocal tract via arrays of sensors. During continuous speech, the location and timing of tongue contacts with the hard palate are recorded hundreds of times per second and a series of electropalatograms are produced for further analyses.

EPG has been used in speech research among normal and clinical populations for decades. For normal populations, this technique has been applied to experimental phonetics research to reveal differences in tongue activity in different phonetic phenomena including the articulatory characterization of different speech sounds produced in different position in a syllable or word, lingual articulation and coarticulation in the world's languages, symmetries of lingual gestures, articulatory timing. and articulatory timing of rate.

In clinical populations, the EPG has been used to both assess and treat speech disorders due to structural abnormality of the vocal tract such as cleft palate, occlusal disorders, glossectomy, functional articulatory disorders, developmental neuromotor disorders and/or acquired neurogenic disorders such as dyspraxia and dysarthria, sensory loss such as hearing impairment, stuttering, laryngectomy, Down syndrome, Parkinson's disease, and such rare conditions as congenital sensory neuropathy.

The pseudo-palate is the main apparatus in EPG; in this technique, a palate insert is mounted in the roof of the mouth. An array of electrodes is attached to the palate insert to capture contact patterns between the tongue and the electrodes hundreds of times per second, allowing rapid tongue-contact patterns overtime during speech to be observed. In a typical device, an array of electrodes are placed on the palate area whose sensing signals are connected by wires to the readout electronics outside of a wearer's mouth. This not only causes discomfort to the wearer, but also compromises natural speech production as the wires interfere with the air pathway and tongue movement. Thickness of many pseudo-palates is as much as 2 mm or thicker, which can further interfere with speech production, as can lack of conformity of the devices to the human palate due to low flexibility of materials used in construction. Furthermore, many known pseudo-palates are expensive to produce and are thus in low demand, causing several models to be discontinued.

Despite advances in the design and construction of pseudo-palate devices, there is still a scarcity of devices that minimally interfere with air pathways during speech and breathing, that conform to the human palate, that are comfortable for the wearer, that incorporate compact electronic systems, that can be constructed for low cost, and that can be integrated with deep learning processes to detect, predict, and quantify brain-related diseases and injuries. These needs and other needs are satisfied by the present disclosure.

SUMMARY

In accordance with the purpose(s) of the present disclosure, as embodied and broadly described herein, the disclosure, in one aspect, relates to a smart pseudo-palate for use in a Smart Electropalatograph (EPG) for Linguistic and Medical Applications (SELMA) system. In one aspect, the pseudo-palate is constructed from a thin, flexible polymer membrane and having an embedded electrode array. The pseudo-palate is configured to detect tongue contacts during speech while causing minimal disturbance or interference with speech motion. The disclosed pseudo-palate in the SELMA system is integrated with a microcontroller, wireless electronic module, and external readout app. The disclosure, in another aspect, relates to integration of the pseudo-palate with a smart sports/health mouth guard containing a series of sensors for monitoring head impacts, body temperature, and heart rate. The SELMA system is capable of automated detection of neurological conditions and brain injury including, but not limited to, concussion, and neurological movement disorders, using acoustic, articulatory, and other biosignals from the device using deep data analysis.

Other systems, methods, features, and advantages of the present disclosure will be or become apparent to one with skill in the art upon examination of the following drawings and detailed description. It is intended that all such additional components, methods, features, and advantages be included within this description be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another and are within the scope of the disclosure described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1A:
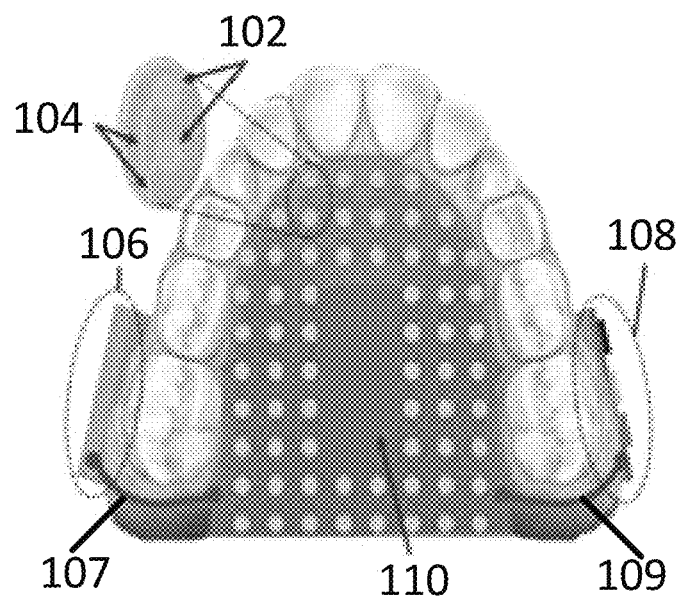
FIG. 1A shows a schematic of a smart pseudo-palate according to one aspect of the present disclosure using a resistive sensing approach.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The pseudo-palate, the SELMA system, and modifications disclosed herein have applications in a variety of fields. Many modifications and other embodiments of the SELMA system disclosed herein will come to mind to one skilled in the art to which the disclosed devices and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any of the methods described herein can be carried out in the order specified or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a flexible material," "an electrode metal," or "a microcontroller," includes, but is not limited to, combinations or mixtures of two or more such flexible materials, electrode metals, or microcontrollers, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

As used herein, "traumatic brain injury" refers to a blow or jolt to the head (i.e., from a sports injury, auto accident, fall, or the like) that causes a disruption in the normal functioning of the brain. Traumatic brain injury (or TBI) can also be caused by a penetrating head injury. In one aspect, a TBI may fall on a spectrum anywhere from a concussion to severe and lasting brain damage. In one aspect, the pseudo-palates disclosed herein are useful for detecting speech patterns associated with TBI prior to the onset of other symptoms.

A "concussion" is one type of TBI. Concussion symptoms can include, but are not limited to, memory problems, problems with balance and coordination, trouble concentrating, headaches, and the like. In one aspect, an early symptom of concussion is altered speech patterns. In a further aspect, the pseudo-palates disclosed herein are useful for detecting these altered speech patterns and thus for early diagnosis of concussions and other TBIs.

A "biomarker" as used herein refers to a measurable parameter indicative of a disease, injury, infection, or the like. Biomarkers can include substances in the blood (i.e., particular proteins) or can include speech, including alterations in speech patterns. In one aspect, the pseudo-palates useful herein can measure changes in speech (e.g., tongue position and pressure) that are useful as biomarkers for early detection of TBI.

"Acoustic information" as used herein refers to properties of speech that can be recorded using audio equipment and analyzed, i.e., sound information. In one aspect, the pseudo-palates disclosed herein allow for measurement of articulatory information that is complementary to acoustic information.

"Articulatory information" as used herein refers to location, size, pressure, and duration of tongue contacts with the hard palate. In one aspect, the pseudo-palates disclosed herein can be used to collect articulatory information. In a further aspect, articulatory information can be used in a complementary fashion with acoustic information for early detection of TBIs and other neurological events.

"Electropalatography" or "EPG" refers to a technique useful for monitoring contact between the tongue and hard palate during speech. In EPG, a "pseudo-palate" is fitted against the wearer's palate. Electrodes in the pseudo-palate record location of tongue contact with palate, size of contact, pressure of the contact, and length of contact. In one aspect, the pseudo-palate disclosed herein is configured to transmit signals from the electrodes to a processing unit that can communicate with an external computer, tablet, or smartphone for analysis of the signals. Thus, in another aspect, the pseudo-palate disclosed herein and its associated accessories are highly portable and can be used, for example, on a sports field in case of suspected injury as well as in a laboratory or medical setting.

Figure 1B:
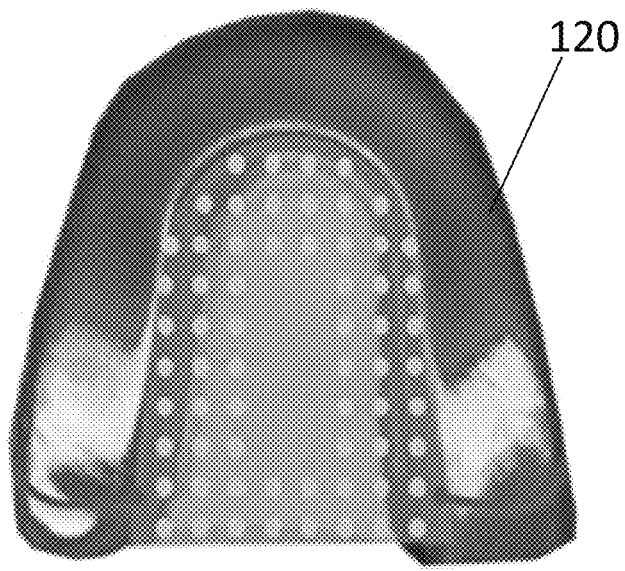
FIG. 1B shows the smart-pseudo palate of FIG. 1A integrated with a smart sports mouth guard.
Figure 2:
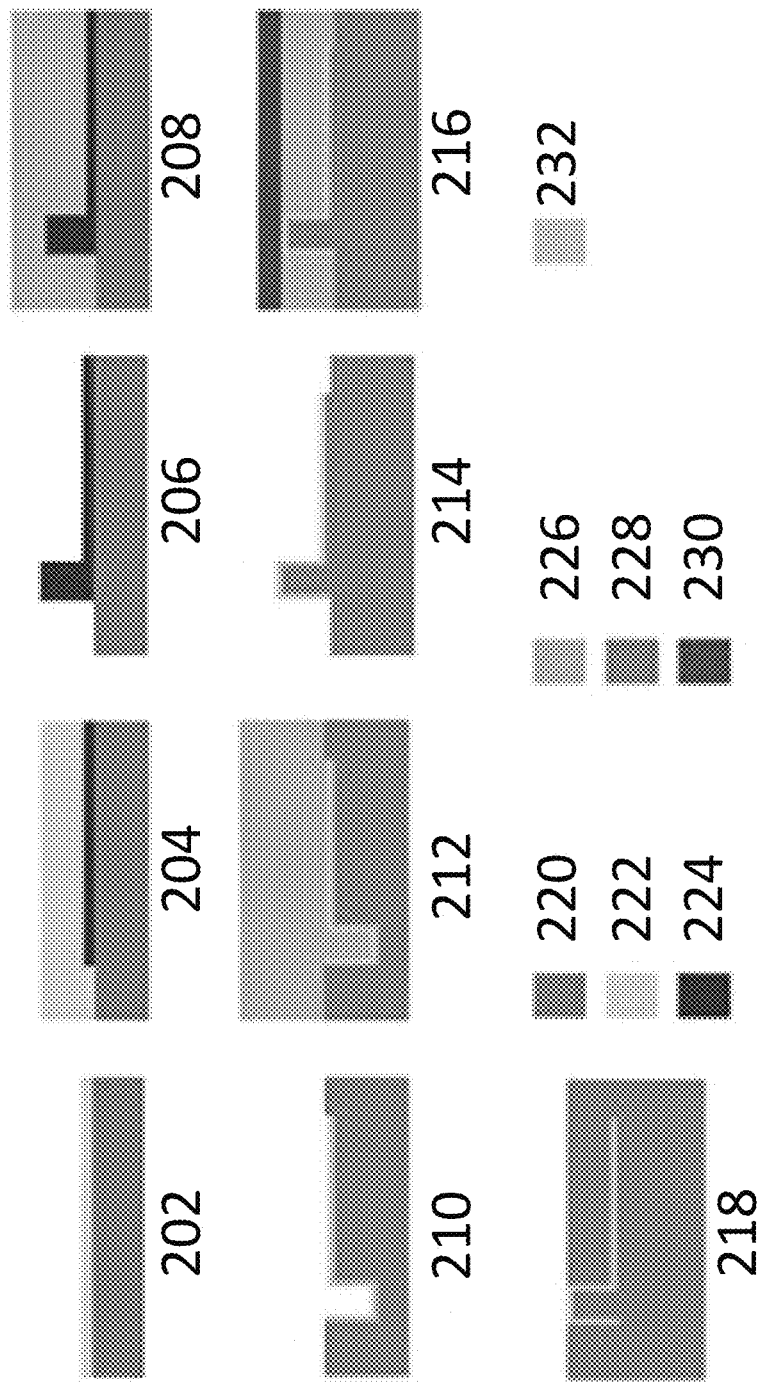
FIG. 2 shows the fabrication process of a pseudo-palate electrode array according to one aspect of the present disclosure using a resistive sensing approach.

In one aspect, as used herein, "resistive sensing" refers to an approach wherein pressure from the tongue compresses a flexible material containing both embedded electrodes and embedded tracing lines or traces (see FIGS. 1A-1B and 2). This compression, in one aspect, closes the gap between the electrodes and tracing lines, which can vary the resistance and actuate the sensor, sending a signal to a microprocessor associated with the position, size, and duration of tongue contact with the pseudo-palate.

In another aspect, as used herein, "capacitive sensing" refers to an approach wherein two electrode layers are separated by a material (e.g., a flexible material) and a capacitance change induced by the change in the gap between the top and bottom electrodes or conditions proximate to the electrode layers can be measured as the tongue contacts various parts of the pseudo-palate during speech. In a further aspect, capacitance at each pixel in the sensing array can be measured and sent to a microprocessor to be assessed to determine position, size, and duration of tongue contact, as well as pressure of tongue contact with the pseudo-palate disclosed herein. "Metal-insulator-metal" or "MIM" capacitive sensing involves an arrangement of two layers of electrodes separated by a flexible material or porous flexible material.

A "flexible material" as used herein refers to a compressible, flexible polymer or polymer system useful for fabrication of the pseudo-palates disclosed herein. In one aspect, the flexible material can be polydimethylsiloxane (PDMS) or porous PDMS, another silicone, polymethylmethacrylate (PMMA), epoxy, polyimide (PI), polyurethane (PU), a hydrogel, cellulose or a cellulose derivative, polyurethane, polyvinyl alcohol, or a combination thereof, or any material capable of containing or being fabricated to contain an array of sensors for a capacitive or resistive sensing approach. In another aspect, the flexible material can be molded or fitted to the palate of a particular user and is comfortable for the user to wear. In still another aspect, the flexible material does not easily rip or tear during speech even if present in a thickness of 200 μm or less.

In yet another aspect, the flexible material is biocompatible.

"Place of articulation" refers, in one aspect, to the location in the mouth of tongue contact wherein the vocal tract is obstructed in order to produce a sound, or to another obstruction (such as, for example, bilabial articulation wherein the lips come together). Various regions of articulation include the epiglottis, pharynx, uvula, soft palate, hard palate, and the like. In one aspect, the pseudo-palates disclosed herein are useful for monitoring palatal articulation.

In one aspect, a "diadochokinetic test" refers to an assessment of how quickly a subject can accurately repeat a series of alternating sounds ("tokens"). In one aspect, a change in diadochokinetic rate is associated with neurodegenerative conditions and/or TBI. In a further aspect, electropalatography and the pseudo-palate disclosed herein can be employed in conjunction with a diadochokinetic test to provide additional biomarkers useful for diagnosing a neurodegenerative condition or injury.

"Phonation" refers to the process by which airflow from the lungs passes through the vocal folds to produce sounds. Phonation can be normal, "breathy" (vocal folds vibrate while they are apart), or "creaky" (posterior portion of vocal folds is held tightly together and anterior portion is slack and vibrating slowly). "Articulation," meanwhile, refers to the formation of clear and distinct sounds in speech. "Respiration" as used herein refers to the act of breathing.

The "speech motor control system" is made up of those systems and organs responsible for the production of speech including, but not limited to, respiration, phonation, and articulation. The respiratory system as well as the larynx, pharynx, tongue, lips, mandible, and soft palate, among other systems and organs, are involved with speech motor control, as well as the basal ganglia and frontal lobes of the brain, which are involved in fine muscle control. In one aspect, some brain injuries as well as neurological disorders such as, for example, Parkinson's disease, can negatively affect the speech motor control system and, thus, the quality of speech produced.

In a further aspect, the pseudo-palate disclosed herein can be used to assess and identify changes in speech and speech motor control at an early stage in cases of suspected brain injury or neurological disorders, potentially leading to earlier and more successful medical interventions.

"Mel-frequency cepstrum coefficients" are used as features in speech recognition systems and can be derived by taking a Fourier transform of an audio signal and performing additional mathematical manipulations to standardize the format of the data.

"Fundamental frequency" as used herein refers to the lowest frequency of a periodic waveform such as, for example, an acoustic wave. "Jitter" refers to movements, variations, or unsteadiness in an electronic signal (i.e., deviation from periodicity of an otherwise periodic signal).

The "random forest classification method" as used herein is a machine learning method using multiple algorithms for classification of data (including, for example, speech sounds and location/duration/pressure of tongue contact with the hard palate). This classification method constructs multiple decision trees at training time and corrects for overfitting data to a training set as can happen when a single decision tree is used. In one aspect, a software application for analysis of data from the pseudo-palate disclosed herein uses the random forest classification method and a suitably large training set in order to diagnose or predict TBI or a neurological disorder based on tongue contacts (e.g., duration, location, size, and pressure) with the pseudo-palate.

"Wireless" as used herein refers to a lack of wired connections between devices such as, e.g., a lack of wires connecting the disclosed pseudo-palate to any device, computer, monitoring equipment, or the like outside the body of the subject wearing the pseudo-palate. Wireless communications can be carried out over wireless links such as, but not limited to, RF, Wi-Fi, Bluetooth®, cellular, or other appropriate wireless technologies. The wireless pseudo-palate disclosed herein can incorporate a microprocessor, wireless communication module, battery, and/or other sensors within the pseudo-palate and include necessary electrical connections to power those devices and read data from them.

Wireless Pseudo-Palate

In one aspect, disclosed herein is a wireless pseudo-palate having arrays of sensing electrodes able to measure both physical and cognitive impacts. In another aspect, the thickness of the pseudo-palate can be from about 0.1 mm to about 2 mm, or can be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 mm, or a combination of any of the foregoing values, or a range encompassing any of the foregoing values. In a further aspect, a thinner pseudo-palate interferes minimally with speech, compared to a thicker pseudo-palate. Further in this aspect, the pseudo-palate can have a thickness of about 0.1 mm.

In some aspects, the pseudo-palate disclosed herein can be integrated with a smart mouth guard for sports. In one aspect, whether the pseudo-palate includes or does not include a sports mouth guard, sensors for pressure, temperature, and inertia, an accelerometer, a gyroscope, a magnetometer, an infrared sensor to monitor impacts, a heart rate monitor, or a combination thereof can be incorporated into or in communication with the pseudo-palate.

In one aspect, when a sports mouth guard is incorporated into the pseudo-palate system, it can be made from a polymeric material including, but not limited to, polymethylmethacrylate (PMMA), ethylene vinyl alcohol (EVA), or a combination thereof. In some aspects, the pseudo-palate can incorporate an additional covering material such as, for example, ethylene vinyl alcohol (EVA), PDMS, PMMA, or a combination thereof. In one aspect, when a smart mouth guard is incorporated into the pseudo-palate system, electronic components can be embedded in EVA (see FIG. 1B). In any of these aspects, sensors and measurement devices incorporated into the pseudo-palate can communicate via a wireless module with a computer, smartphone, or tablet for data analysis.

The disclosed pseudo-palate offers numerous benefits compared to current devices. In one aspect, the thickness of the palate membrane can be about 100 µm, which is about one-twentieth of a typical pseudo-palate thickness. In a further aspect, a thin palate membrane minimizes the blockage of air flow during speech production. In another aspect, the pseudo-palate can be constructed from a biocompatible, flexible material such as, for example, polydimethylsiloxane (PDMS), so as to better conform to the palate of the subject using the pseudo-palate. Further in this aspect, a flexible pseudo-palate is more comfortable for the wearer.

In one aspect, the pseudo-palate is fabricated using a facile, micromolding-based process in which the flexible material and the electrodes are seamlessly integrated. In still another aspect, the pseudo-palate incorporates compact electronic systems including a microprocessor, a wireless module, and a battery. Further in this aspect, the electronic systems are located on the outside wall of the upper gum of the pseudo-palate so as not to disturb air pathways during speech. In a further aspect, having an integrated wireless microprocessor can convert sensed signals to quantified information, minimizing data transfer required. In one aspect, the electronic components of the pseudo-palate can be wirelessly charged. Further in this aspect, the electronics in the pseudo-palate are hermetically sealed.

In another aspect, the pseudo-palate has lower costs to produce than those of known devices, several of which have been discontinued due to manufacturing costs. In one aspect, manufacturing cost is low enough that the pseudo-palate can be considered as disposable.

In one aspect, either resistive sensing or capacitive sensing can be used in the pseudo-palates disclosed herein. In a further aspect, resistive sensing may be more useful for simple fabrication of devices capable of capturing the position, size, and duration of tongue contacts with the palate. In an alternative aspect, capacitive sensing may be more useful for fabrication of comprehensive devices capable of capturing the position, size, duration, and pressure of tongue contacts with the palate.

Features and Fabrication Process for Wireless Pseudo-Palate

Turning now to the drawings, FIG. 1A shows a schematic of an example of a smart pseudo-palate constructed using a resistive sensing approach according to one aspect of the present disclosure. Embedded in the polydimethylsiloxane (PDMS) 110 palate are electrodes 102 and/or tracing lines (or traces) 104. Battery 106 and wireless microprocessor module 108 can be located at the outer gums in the posterior portion of the mouth in order to provide minimal interference to airflow and tongue movement. Also shown are a first wire 109 electrically connected to the plurality of tracing lines and extending from the posterior end of the flexible material and adapted to surround a first posterior-lateral corner of the subject's upper gum to electrically connect to the wireless module 108 and a second wire 107 electrically connected to the plurality of tracing lines and extending from the posterior end of the flexible material and adapted to surround a second posterior-lateral corner of the subject's upper gum opposite to the first posterior-lateral corner to electrically connect to the battery 106.

FIG. 1B shows the smart pseudo-palate of FIG. 1A integrated with a smart sports mouth guard 120 that can be made from EVA or another biocompatible polymeric material. In one aspect, the pseudo-palate includes 64 detecting electrodes 102. Other numbers of electrodes are also envisioned including, but not limited to, 128, 256, 512, 1024, 2048, or 4096 electrodes. In another aspect, the electrodes and tracing lines 104 can be fabricated from gold, titanium, platinum, nickel, chromium, copper, silver, another metal, or a combination thereof. In one aspect, the diameter of a typical electrode 102 can be from about 100 μm to about 1 mm, or can be about 100, 200, 300, 400, 500, 600, 700, 800, or 900 μm, or about 1 mm, or a combination of any of the foregoing values, or a range encompassing any of the foregoing values, and the line width of embedded tracing lines 104 can be from about 5 μm to about 50 μm, or can be about 5, 10, 15, 20, 25, 30, 35, 40, 45, or about 50 μm, or a combination of any of the foregoing values, or a range encompassing any of the foregoing values.

FIG. 2 shows an example of a fabrication process of a pseudo-palate electrode array according to one aspect of the present disclosure. In this process, a first photocurable epoxy coating 222 is spin coated on a glass or silicon substrate 220 with, e.g., from about a 5 μm to about a 500 μm thickness, or at about a 5, 25, 50, 75, 100, 150, 200, 250, 300, 350, 400, 450, or about 500 μm thickness, or a combination of any of the foregoing values, or a range encompassing any of the foregoing values. In one aspect, the photocurable epoxy is spin coated at a 10 μm thickness at 202. In a further aspect, the photocurable epoxy can be SU-8 or another photocurable epoxy. In some aspects, a photocurable polyimide (PI) or photocurable polyurethane (PU) can also be used instead of or in addition to the photocurable epoxy. In any of these aspects, curing time and temperature can vary depending on the polymer. In one aspect, curing time is from about 10 min to about 3 hours, or is about 10, 20, 30, 40, or 50 min, or about 1, 1.5, 2, 2.5, or 3 hours, or a combination of any of the foregoing values, or a range encompassing any of the foregoing values. In one aspect, curing can occur at about 95° C. A line trace is photolithographically patterned and developed in the cured epoxy 224. A second photocurable epoxy coating 222 can be spin coated at, e.g., from about 10 μm to about 200 μm thickness, or about 10, 25, 50, 75, 100, 125, 150, 175, or about 200 μm thickness, or a combination of any of the foregoing values, or a range encompassing any of the foregoing values. In one aspect, the second coating has about a 50 μm thickness on top of the cured epoxy 224 at 204. The second photocurable epoxy coating is cured 224 after being photolithographically patterned and developed for the electrodes at 206. At 208, PDMS 226 is cast on top of the cured epoxy layers 224 and cured at 70° C. for 2 h 208. The cured PDMS 228 can them be removed. At 210, a gold layer 232 with a thickness of, e.g., about 200 nm can be conformally coated using sputtering on the cured PDMS 228. The top portion of the gold 232 can be removed by pattern transfer using tape stamping 210. Following this, PDMS 226 with a thickness of, e.g., about 40 μm is spin coated on top of the existing structures and is cured, e.g., at 70° C. for 2 h at 212. Upon the separation of the first and second PDMS layers, the thin gold layer 232 is transferred from the first PDMS layer to the second PDMS layer using the 3D pattern transfer molding process at 214. A glass substrate 230 can be capped on the electrode area at 216 and the gap between the glass cap and the cured PDMS 228 is filled with additional PDMS 226, which can then be cured, e.g., at 70° C. for 2 h at 216. The removal of the glass cap layer 230 at 218 completes a thin PDMS layer embedded with an electrode array for resistive sensing. The mold master formed at 206 can be used repeatedly.

Figure 3:
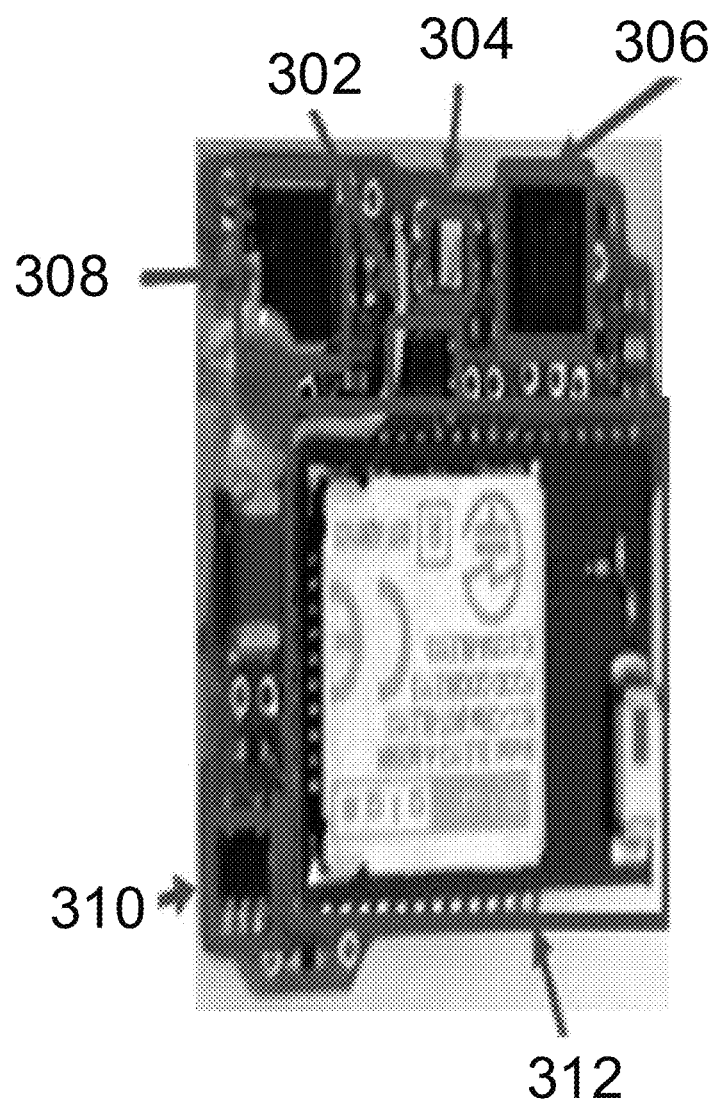
FIG. 3 shows a wireless module useful in conjunction with the smart pseudo-palate using a resistive sensing approach disclosed herein.

FIG. 3 shows an example of a wireless module useful in conjunction with the smart pseudo-palate disclosed herein. The wireless module comprises processing circuitry including a voltage regulator 302, switch 304, inertia sensor 306, data converter 308, temperature sensor 310, and microcontroller 312. Sensing, microprocessor, and wireless transceiver (TX/RX) circuitry can be powered by a battery and/or supercapacitor. In some aspects, when the system must be used for an extended period of time, a wireless power transfer and charging module with a rechargeable battery can be included, or a commercial battery can be used such as, for example, a LiPo battery initially developed for use with SKY Hawkeye quadcopters (drones). In another aspect, an ultra-low power and fully integrated power management unit with impedance matching circuits can be designed and fabricated using a complementary metal oxide semiconductor (CMOS) process. In one aspect, the overall footprint of the processing circuitry of FIG. 3 is about 11×18 mm. In another aspect, data readout applications can be implemented in Android and iOS smartphone operating systems.

Figure 4:
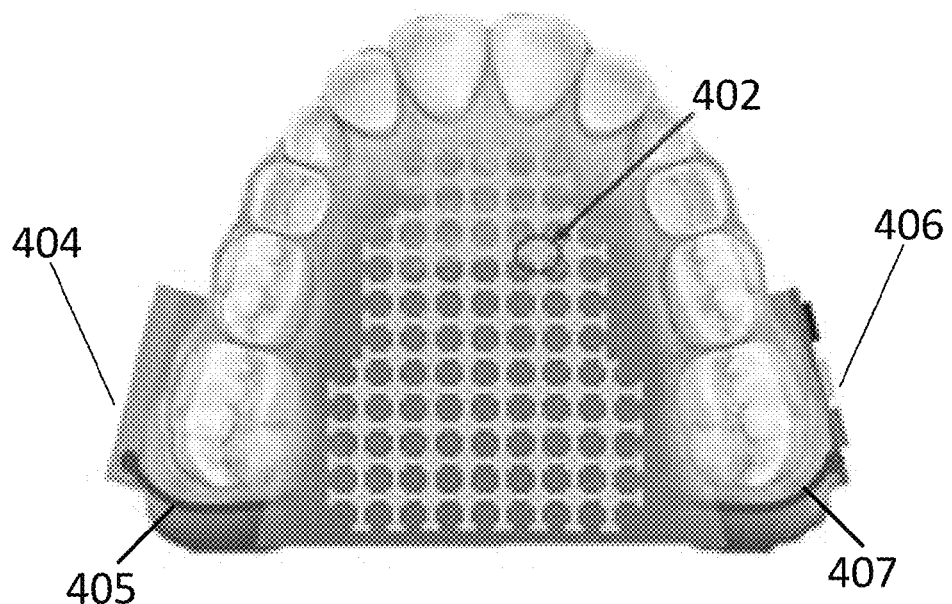
FIG. 4 shows a schematic of a pseudo-palate according to one aspect of the present disclosure having a capacitive sensing array including capacitive sensing unit pixel. Also shown is placement of battery and wireless module useful for operation of the pseudo-palate.

FIG. 4 shows a schematic of a pseudo-palate according to one aspect of the present disclosure having a capacitive sensing array including capacitive sensing unit pixels 402. In one aspect, overall electrode placement similar to that of resistive sensing can be used. In a further aspect, the sensing method can be metal-insulator-metal (MIM) capacitive sensing. Also shown is an example of the placement of a battery 404 and wireless module 406 useful for operation of the pseudo-palate. Also shown are a first wire 407 electrically connected to the top array of electrodes and the bottom array of electrodes and extending from the posterior end of the flexible material and adapted to surround a first posterior-lateral corner of the subject's upper gum to electrically connect to the wireless module 406 and a second wire 405 electrically connected to the top array of electrodes and the bottom array of electrodes and extending from the posterior end of the flexible material and adapted to surround a second posterior-lateral corner of the subject's upper gum opposite to the first posterior-lateral corner to electrically connect to the battery 404.

Figure 5:
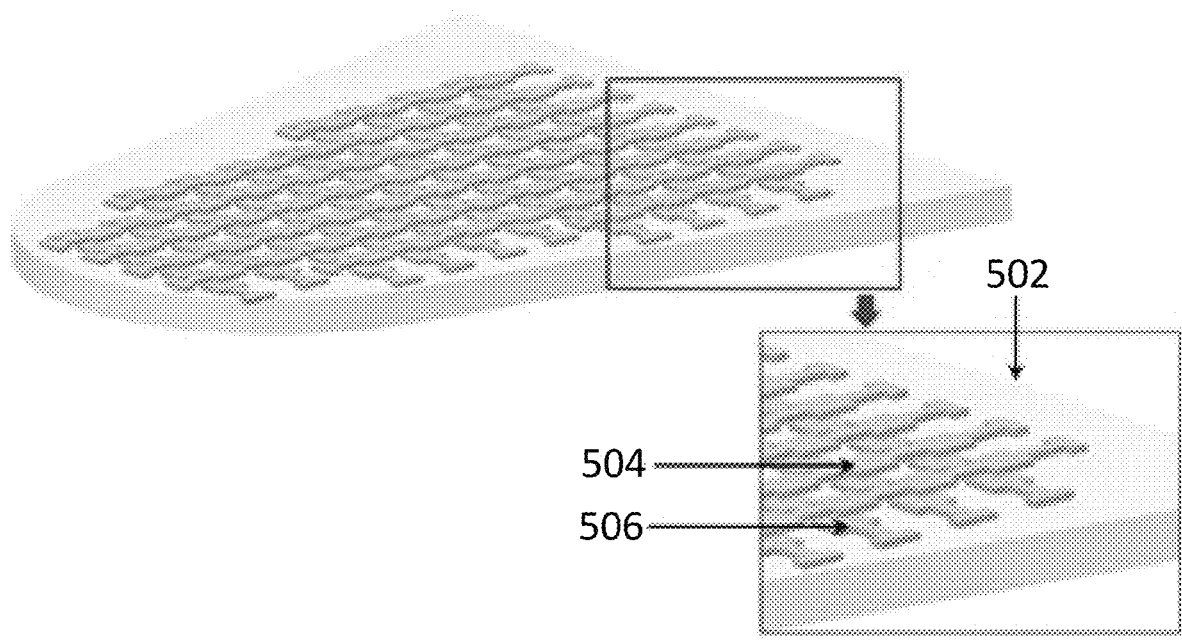
FIG. 5 shows a perspective view of the capacitive sensing electrode array of the pseudo-palate of FIG. 4 embedded in the PDMS pseudo-palate membrane.

FIG. 5 shows a perspective view of the capacitive sensing electrode array of the pseudo-palate of FIG. 4 embedded in the PDMS pseudo-palate membrane 502 including overlaying top electrodes 504 and bottom electrodes 506. In one aspect, the thickness of the PDMS insulator layer can be from about 10 to about 100 μm, or can be about 10, 20, 30, 40, 50, 60, 70, 80, 90, or about 100 μm, or a combination of any of the foregoing values, or a range encompassing any of the foregoing values. In another aspect, the nominal thickness of the top and bottom metal layers can independently be from about 50 to about 200 nm, or can be about 50, 60, 70, 80, 90, 100, 110, 120, 130, 140, 150, 160, 170, 180, 190, or about 200 nm, or a combination of any of the foregoing values, or a range encompassing any of the foregoing values. In a further aspect, each capacitor cell can detect contact and pressure levels produced by tongue touching during speech production. In a further aspect, the basic capacitive-sensing mechanism measures the capacitance change induced by the change in the gap between the top and bottom electrodes 504 and 506. In one aspect, when the tongue touches the surface of the palate, applying pressure, the gap between the two metal plates decreases and capacitance increases. In any of these aspects, the gap between electrodes is filled with the PDMS in which the electrodes are embedded. In some aspects, the PDMS filling the gap is porous. In a further aspect, by measuring capacitance for all of the pixels in the capacitive array, tongue contact position and applied pressure levels can be determined.

Figure 6:
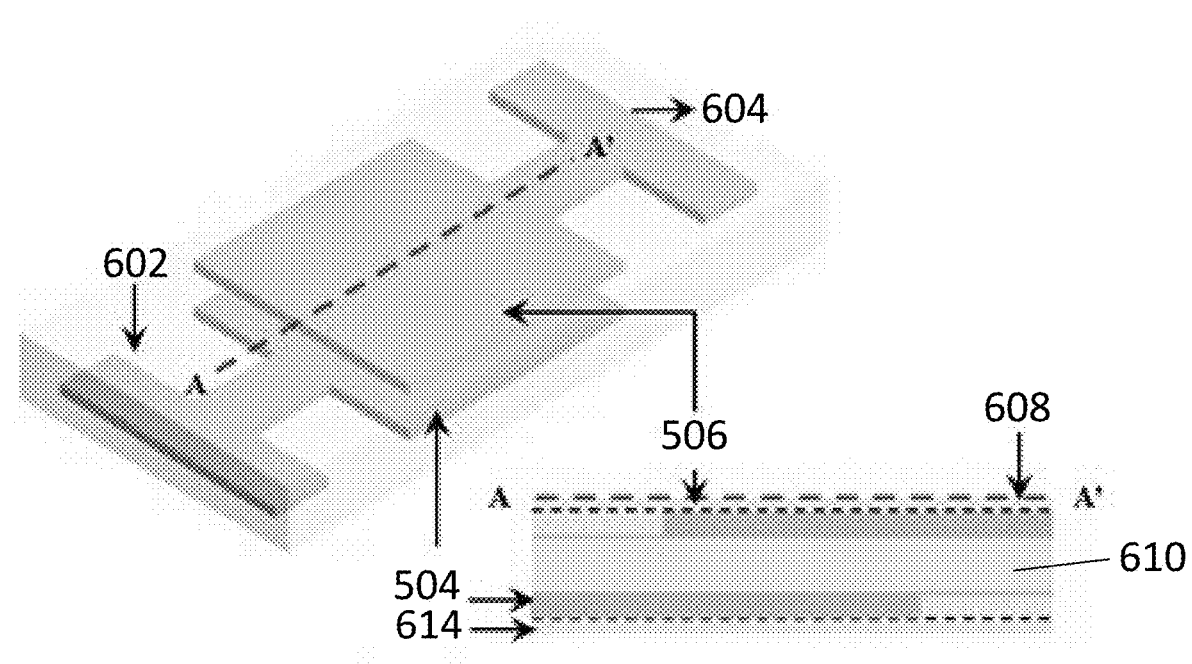
FIG. 6 shows a schematic of a unit pixel of a capacitive sensing array of the pseudo-palate of FIG. 4 embedded in the PDMS pseudo-palate membrane disclosed herein.

FIG. 6 shows a schematic of a unit pixel of a capacitive sensing array of the pseudo-palate of FIGS. 4 and 5 embedded in the PDMS pseudo-palate membrane disclosed herein. Bottom probing electrode 602 forming a portion of the bottom electrodes 504 and top probing electrode 604 forming a portion of the top electrodes 506 are embedded in the PDMS including top overcoat PDMS layer 608, bottom overcoat PDMS layer 614, and intermediate dielectric PDMS layer 610.

A cross-sectional view of the electrodes is shown along line A-A' is shown in FIG. 6. The distance between the top and bottom probing electrodes, 602 and 604, respectively, can change during pseudo-palate usage. In a further aspect, layers 608 and 614 can independently have a thickness in a range from about 50 to about 100 µm, or can be about 50, 60, 70, 80, 90, or about 100 µm, or a combination of any of the foregoing values, or a range encompassing any of the foregoing values. In one aspect, the total thickness of the capacitive sensing pseudo-palate disclosed herein is from about 60 to about 200 µm, or is about 60, 70, 80, 90, 100, 110, 120, 130, 140, 150, 160, 170, 180, 190, or about 200 µm, or a combination of any of the foregoing values, or a range encompassing any of the foregoing values.

Figure 13A:
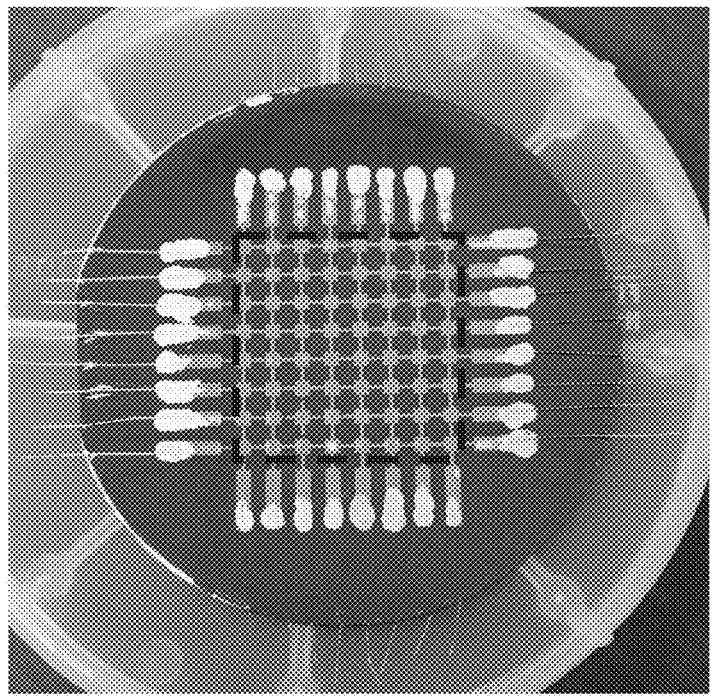
FIGS. 13A-13B show exemplary fabricated pseudo-palates on a silicone substrate. Squares outlined by blue dashed lines show the capacitive sensing array depicted in FIG. 5. Squares outlined in red show single electrodes depicted in FIG. 6.
Figure 13B:
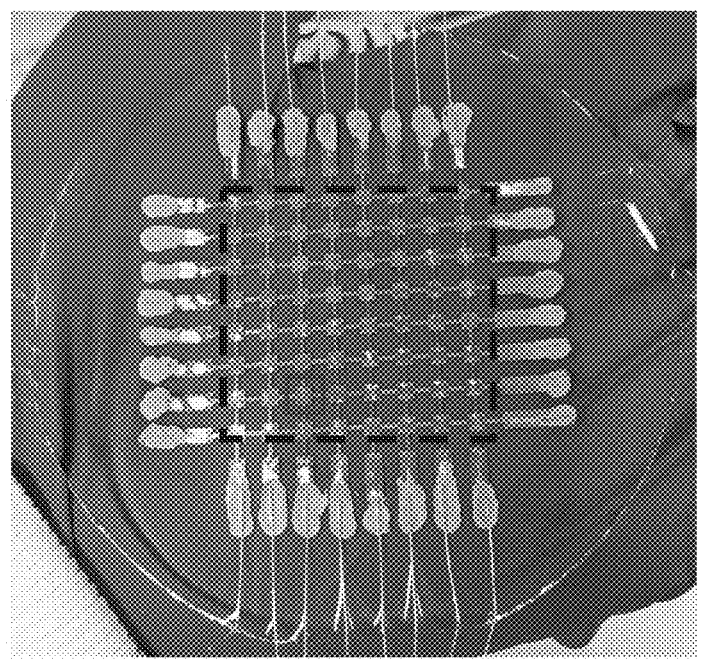

Exemplary fabricated devices are shown in FIGS. 13A-13B.

Figure 7:
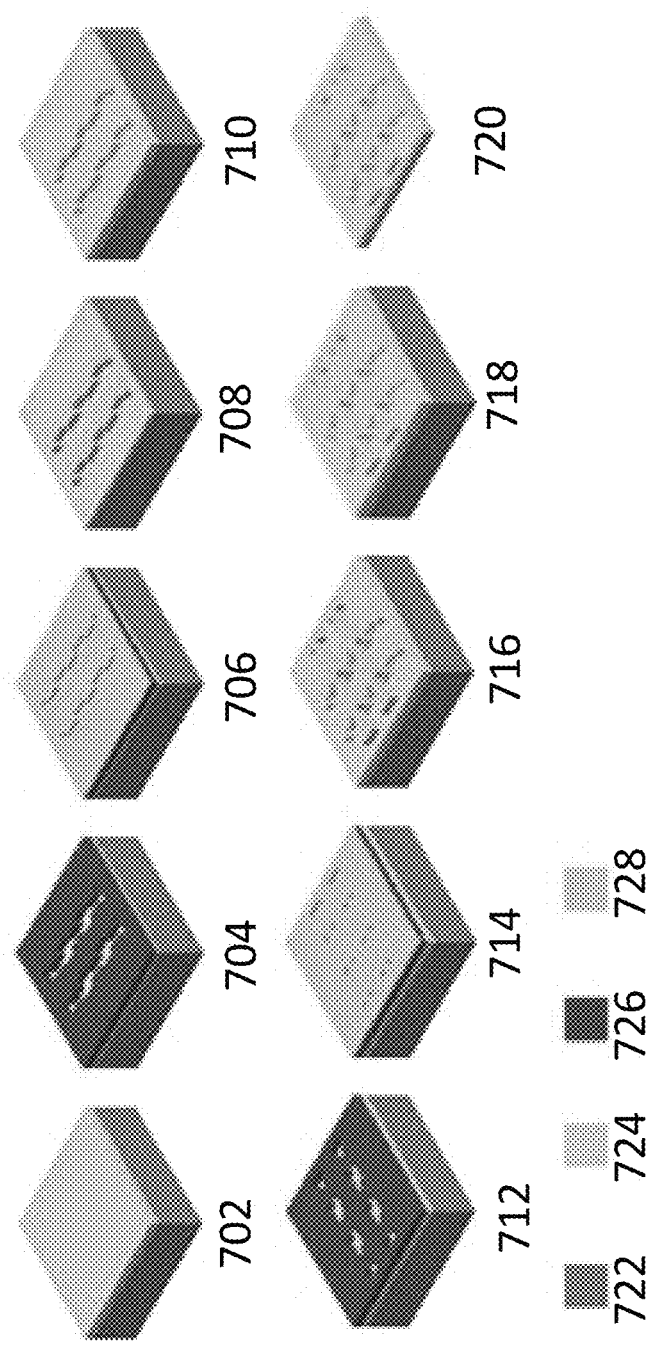
FIG. 7 shows a fabrication process useful for constructing the pseudo-palates using a capacitive sensing approach disclosed herein.

FIG. 7 shows a fabrication process useful for constructing the pseudo-palate disclosed herein. First, on a prepared silicon/glass substrate 722, liquid PDMS 724 and curing agent are mixed and placed in a low-pressure chamber to remove air bubbles generated during mixing; the mixture is spin-coated on the substrate 722, wherein the thickness of the PDMS layer 724a depends on the spinning speed of the spin center. and following spin-coating, the coated sample is placed in a convection oven for curing at 702. In one aspect, the PDMS can be a commercial PDMS such as, for example, DOWSIL 184 Silicone Elastomer Base (Dow Corning, Inc.) and the curing agent can be DOWSIL 184 Silicone Elastomer Curing Agent (Dow Corning, Inc.). In some aspects, the PDMS and curing agent are packaged as a kit. Kits useful herein include that sold under the trade name SYLGARD™ 184 (Dow Corning, Inc.) Next, a conventional photolithography process is performed in which a photoresist 726a is coated on the cured PDMS surface and the bottom electrode array is patterned at 704. In some aspects, a shadow mask with a pattern can be used as an alternative to photolithography. Next, a target metal 728a such as, for example, titanium, gold, platinum, nickel, chromium, copper, silver, or a combination thereof can be deposited at 706. In one aspect, the metal can have a thickness of, e.g., between about 30 and about 200 nm, or of about 30, 40, 50, 60, 70, 80, 90, 100, 110, 120, 130, 140, 150, 160, 170, 180, 190, or about 200 nm, or a combination of any of the foregoing values, or a range encompassing any of the foregoing values. The photoresist 726a can be selectively removed with a solvent ("lift-off process"), thus patterning the bottom electrode array at 708. In one aspect, the solvent can be acetone. The intermediate dielectric PDMS layer 724b can then be spin coated at 710. In some aspects, a porous PDMS 724 can be used. Without wishing to be bound by theory, a porous PDMS may lead to lower mechanical elasticity and higher sensitivity. Further in this aspect, a uniform and smooth coating can be very beneficial for consistent sensing. Following spin coating, a second photolithography process is performed with photoresist 726b at 712, followed by a second metal deposition process to form the top electrode array from metal 728b at 714 and a second lift-off process leaving the top electrode array at 716. In one aspect, the second metal layer can be gold, titanium, platinum, nickel, chromium, copper, silver, another metal, or a combination thereof, and can have a thickness of between about 30 and about 200 nm, or of about 30, 40, 50, 60, 70, 80, 90, 100, 110, 120, 130, 140, 150, 160, 170, 180, 190, or about 200 nm, or a combination of any of the foregoing values, or a range encompassing any of the foregoing values. In one aspect, alignment between the upper and lower electrode patterns can be important to the operation of the fabricated device. Finally, the top passivation PDMS layer 724c is spin-coated and cured at 718 and the fabricated device is peeled off from the substrate at 720, completing the fabrication process (720). In FIG. 7, each PDMS layer 724 is represented by a blue color, photoresists 726 by a red color, and metal 728 by a gold color.

Figure 8:
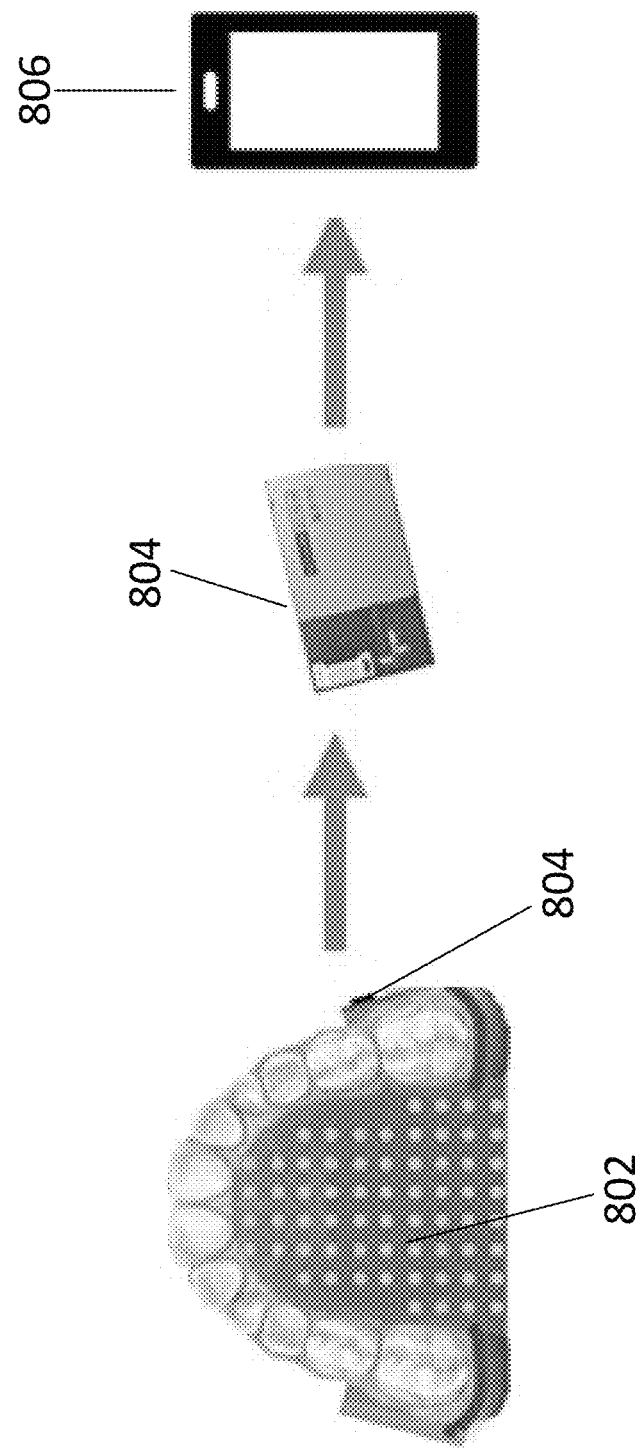
FIG. 8 is a schematic of a configuration for wireless data acquisition from the pseudo-palate disclosed herein.

FIG. 8 is a schematic of a configuration for wireless data acquisition from the pseudo-palate disclosed herein. Sensors 802 are in communication with, e.g., a Bluetooth-integrated microcontroller 804, which can collect data and communicate it wirelessly to a processing device such as, e.g., a computer, smartphone, or tablet 806 for processing. The microcontroller 804 can be included in the wireless microprocessor module 108 of FIG. 1A or 406 of FIG. 4 or the wireless module of FIG. 3. In one aspect, wireless signals can be transferred up to about 10 m (or farther) though a wireless communication link.

Figure 9:
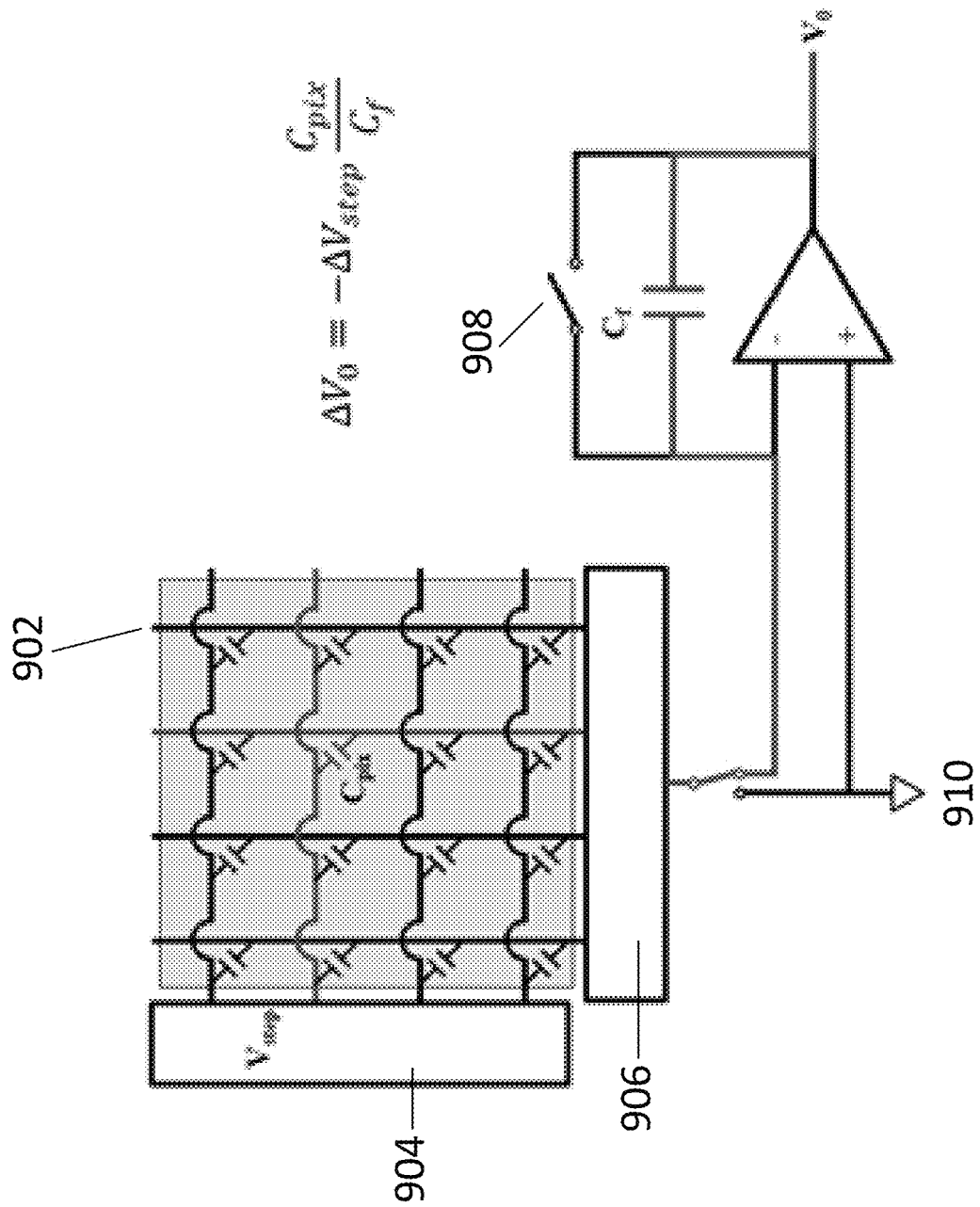
FIG. 9 shows a schematic of a sensing readout scheme according to one aspect of the present disclosure.

FIG. 9 shows a schematic of a sensing readout scheme according to one aspect of the present disclosure. Capacitive electrodes in the same row or column of sensor 902 are connected electrically with straight-line interconnects for the readout of sensing signals. The electrodes of all the rows are formed in the same level, e.g., the bottom electrodes in FIG. 6 and the electrodes of all the columns are formed from the top electrodes in FIG. 6. By switching the row 906 and column 904 in high speed, it can measure the contact location and the pressure levels of the overall electrode array in real time. The sensing procedure is that first each pixel capacitor $C_{pix}$ is selected by a row decoder and reset 908. Then $V_{step}$ is applied, the $C_{pix}$ is charged. When the pixel is selected by a column decoder, the stored charge is transferred to the feedback capacitance ($C_f$) producing output voltage Vo. The output voltage can be amplified by the ratio between $C_{pix}$ and $$C_f, \text{i.e. } \Delta V_o = -\Delta V_{step} \frac{C_{pix}}{C_f}.$$

A virtual ground 910 is also shown. In one aspect, the measured voltage can be translated to a corresponding capacitance and pressure using a prepared lookup table. In a further aspect, using a Python coded graphical user interface, the extracted pressure information can be displayed on a pseudo-palate map. In one aspect, the pressure information can be displayed using grayscale. In alternative aspect, the pressure information can be displayed using color graphics.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

ASPECTS

The present disclosure can be described in accordance with the following numbered Aspects, which should not be confused with the claims.

Aspect 1. A pseudo-palate for resistive sensing of tongue contacts with a subject's hard palate, the pseudo-palate comprising a plurality of detecting electrodes and a plurality of tracing lines connecting the electrodes, wherein the electrodes and tracing lines are embedded in a flexible material.

Aspect 2. The pseudo-palate of aspect 1, wherein the electrodes comprise gold, titanium, platinum, chromium, nickel, copper, silver, or a combination thereof.

Aspect 3. The pseudo-palate of aspect 1 or 2, wherein the electrodes are from about 100 µm to about 1 mm in diameter.

Aspect 4. The pseudo-palate of aspect 1 or 2, wherein the electrodes are about 1 mm in diameter.

Aspect 5. The pseudo-palate of any of aspects 1-4, wherein the pseudo-palate comprises from about 64 to about 4096 electrodes.

Aspect 6. The pseudo-palate of any of aspects 1-4, wherein the pseudo-palate comprises 64 electrodes.

Aspect 7. The pseudo-palate of any of aspects 1-6, wherein the tracing lines comprise gold, titanium, platinum, nickel, copper, silver, or a combination thereof.

Aspect 8. The pseudo-palate of any of aspects 1-7, wherein the tracing lines comprise a width of from about 5 µm to about 50 µm.

Aspect 9. The pseudo-palate of any of aspects 1-7, wherein the tracing lines comprise a width of about 50 µm.

Aspect 10. The pseudo-palate of any of aspects 1-9, wherein the flexible material comprises polydimethylsiloxane (PDMS), porous PDMS, polymethylmethacrylate (PMMA), polyimide (PI), polyurethane (PU), epoxy, or a combination thereof.

Aspect 11. The pseudo-palate of any of aspects 1-10, wherein the pseudo-palate is from about 0.1 mm to 2 mm in thickness.

Aspect 12. The pseudo-palate of any of aspects 1-10, wherein the pseudo-palate is about 0.1 mm thick.

Aspect 13. The pseudo-palate of any of aspects 1-12, further comprising a microprocessor, a wireless communication module, and a battery.

Aspect 14. The pseudo-palate of aspect 13, wherein the microprocessor, wireless communication module, and battery are positioned on an outside wall of the subject's upper gums.

Aspect 15. The pseudo-palate of any of aspects 1-14, further comprising a mouth guard.

Aspect 16. The pseudo-palate of aspect 15, wherein the mouth guard comprises polymethylmethacrylate (PMMA), ethylene vinyl alcohol (EVA), or a combination thereof.

Aspect 17. The pseudo palate of any of aspects 1-16, further comprising a pressure sensor, a temperature sensor, an inertia sensor, an accelerometer, a gyroscope, a magnetometer, an infrared sensor for monitoring impacts, a heart rate monitor, or a combination thereof.

Aspect 18. The pseudo-palate of any of aspects 1-17, further comprising a covering material.

Aspect 19. The pseudo-palate of aspect 18, wherein the covering material comprises an ethylene vinyl alcohol polymer, polymethylmethacrylate (PMMA), polydimethylsiloxane (PDMS), or a combination thereof.

Aspect 20. The pseudo-palate of any of the preceding aspects, wherein the pseudo-palate is disposable.

Aspect 21. A pseudo-palate for capacitive sensing of tongue contacts with a subject's hard palate, the pseudo-palate comprising a top electrode array and a bottom electrode array, wherein the top and bottom electrode arrays are embedded in a flexible material, wherein the pseudo-palate, when worn by the subject, is oriented such that the top electrode array is close to the subject's hard palate than the bottom electrode array, and wherein the top and bottom electrode arrays are separated by a gap.

Aspect 22. The pseudo-palate of aspect 21, wherein the top electrode array and the bottom electrode array comprise gold, titanium, platinum, nickel, chromium, copper, silver, or a combination thereof.

Aspect 23. The pseudo-palate of aspect 21 or 22, wherein the top electrode array and the bottom electrode array are, independently, from about 50 to about 200 nm in thickness.

Aspect 24. The pseudo-palate of aspect 21 or 22, wherein the top electrode array and the bottom electrode array are, independently, from about 100 to about 200 nm in thickness.

Aspect 25. The pseudo-palate of any of aspects 21-24, wherein the flexible material comprises polydimethylsiloxane (PDMS), porous PDMS, polymethylmethacrylate (PMMA), polyimide (PI), polyurethane (PU), epoxy, or a combination thereof.

Aspect 26. The pseudo-palate of any of aspects 21-25, wherein the pseudo-palate is from about 0.1 mm to 2 mm in thickness.

Aspect 27. The pseudo-palate of any of aspects 21-25, wherein the pseudo-palate is about 0.1 mm thick.

Aspect 28. The pseudo palate of any of aspects 21-27, wherein the gap comprises a polydimethylsiloxane insulator layer.

Aspect 29. The pseudo-palate of aspect 28, wherein the polydimethylsiloxane insulator layer is from about 10 to about 100 µm in thickness.

Aspect 30. The pseudo-palate of any of aspects 21-29, further comprising a microprocessor, a wireless communication module, and a battery.

Aspect 31. The pseudo-palate of aspect 30, wherein the microprocessor, wireless communication module, and battery are positioned on an outside wall of the subject's upper gums.

Aspect 32. The pseudo palate of any of aspects 21-31, further comprising a pressure sensor, a temperature sensor, an inertia sensor, an accelerometer, a gyroscope, a magnetometer, an infrared sensor for monitoring impacts, a heart rate monitor, or a combination thereof.

Aspect 33. The pseudo palate of any of aspects 21-32, wherein the pseudo-palate is disposable.

Aspect 34. A method for making an electrode array for resistive sensing of tongue contacts with a subject's hard palate, the method comprising:
(a) applying a first coating to a substrate and curing the first coating;
(b) photolithographically patterning and developing a line trace on the first coating;
(c) applying a second coating over the first coating and the line trace, and curing the second coating;
(d) casting a first flexible polymer over the second coating and curing the first flexible polymer;
(e) sputter coating a metal layer over the flexible polymer;
(f) removing a portion of the metal layer;
(g) applying a second flexible polymer over the metal layer and curing the second flexible polymer;

(h) separating the first flexible polymer from the second flexible polymer, wherein the metal layer adheres to the second flexible polymer;
(i) applying a cap to the metal layer, wherein a gap is created between the cap and the metal layer;
(j) filling the gap with a third flexible polymer and curing the third flexible polymer; and
(k) removing the cap to reveal an electrode array comprising the metal layer sandwiched between the second and third flexible polymers.

Aspect 35. The method of aspect 34, wherein the first coating comprises photocurable epoxy, photocurable polyimide (PI), photocurable polyurethane (PU), or a combination thereof.

Aspect 36. The method of aspect 34 or 35, wherein the first coating is applied by spin coating.

Aspect 37. The method of any of aspects 34-36, wherein the first coating has a thickness of from about 10 to about 200 μm.

Aspect 38. The method of any of aspects 34-36, wherein the first coating has a thickness of about 10 μm.

Aspect 39. The method of any of aspects 34-38, wherein the substrate comprises glass, silicon, or a combination thereof.

Aspect 40. The method of any of aspects 34-39, wherein the second coating comprises photocurable epoxy, photocurable polyimide, photocurable polyurethane, or a combination thereof.

Aspect 41. The method of any of aspects 34-40, wherein the second coating is applied by spin coating.

Aspect 42. The method of any of aspects 34-41, wherein the second coating has a thickness of from about 10 μm to about 200 μm.

Aspect 43. The method of any of aspects 34-41, wherein the second coating has a thickness of about 50 μm.

Aspect 44. The method of any of aspects 34-43, wherein the first flexible polymer comprises polydimethylsiloxane (PDMS), porous PDMS, polymethylmethacrylate (PMMA), polyimide (PI), polyurethane (PU), epoxy, or a combination thereof.

Aspect 45. The method of any of aspects 34-44, wherein the first flexible polymer is cured at about 70° C. for about 2 h.

Aspect 46. The method of any of aspects 34-45, wherein the metal layer comprises gold, titanium, platinum, nickel, chromium, copper, silver, or a combination thereof.

Aspect 47. The method of any of aspects 34-46, wherein the metal layer has a thickness of about 200 nm.

Aspect 48. The method of any of aspects 34-47, wherein the portion of metal layer is removed by pattern transfer using tape stamping.

Aspect 49. The method of any of aspects 34-48, wherein the second flexible polymer comprises polydimethylsiloxane (PDMS), porous PDMS, polymethylmethacrylate (PMMA), polyimide (PI), polyurethane (PU), epoxy, or a combination thereof.

Aspect 50. The method of any of aspects 34-49, wherein the second flexible polymer is cured at about 70° C. for about 2 h.

Aspect 51. The method of any of aspects 34-50, wherein the second flexible polymer has a thickness of about 40 μm.

Aspect 52. The method of any of aspects 34-51, wherein the cap comprises glass.

Aspect 53. The method of any of aspects 34-52, wherein the third flexible polymer comprises polydimethylsiloxane (PDMS), porous PDMS, polymethylmethacrylate (PMMA), polyimide (PI), polyurethane (PU), epoxy, or a combination thereof.

Aspect 54. The method of any of aspects 34-53, wherein the third flexible polymer is cured at about 70° C. for about 2 h.

Aspect 55. A method for making a dual electrode array for capacitive sensing of tongue contacts with a subject's hard palate, the method comprising:
(a) mixing a first flexible polymer and a curing agent to form a first mixture;
(b) applying the first mixture to a substrate and curing the first mixture;
(c) applying a pattern for a bottom electrode array using a first shadow mask or a first photoresist followed by photolithography;
(d) depositing a first metal to create the bottom electrode array;
(e) removing the first shadow mask or the first photoresist;
(f) applying a second flexible polymer to the first mixture and bottom electrode array and curing the second flexible polymer;
(g) applying a pattern for a top electrode array using a second shadow mask or a second photoresist followed by photolithography;
(h) depositing a second metal to create the top electrode array;
(i) removing the second shadow mask or the second photoresist;
(j) applying a third flexible polymer to the second flexible polymer and top electrode array and curing the third flexible polymer;
(k) removing the substrate.

Aspect 56. The method of aspect 55, further comprising degassing the first mixture prior to performing step (b).

Aspect 57. The method of aspect 56, wherein degassing the first mixture is accomplished in a low pressure air chamber.

Aspect 58. The method of any of aspects 55-57, wherein the first flexible polymer comprises polydimethylsiloxane (PDMS), porous PDMS, polyimide (PI), polymethylmethacrylate (PMMA), polyurethane (PU), and combinations thereof.

Aspect 59. The method of any of aspects 55-58; wherein the first mixture is applied to the substrate by spin coating.

Aspect 60. The method of any of aspects 55-59, wherein the substrate comprises silicon, glass, or a combination thereof.

Aspect 61. The method of any of aspects 55-60, wherein the first metal comprises gold, titanium, platinum, nickel, chromium, copper, silver, or a combination thereof.

Aspect 62. The method of any of aspects 55-61, wherein the first metal is deposited with a thickness of from about 30 to about 200 nm.

Aspect 63. The method of any of aspects 55-62, wherein the first photoresist is removed using a solvent.

Aspect 64. The method of aspect 63, wherein the solvent comprises acetone.

Aspect 65. The method of any of aspects 55-64, wherein the second flexible polymer comprises polydimethylsiloxane (PDMS), porous PDMS, polymethylmethacrylate (PMMA), polyimide (PI), polyurethane (PU), epoxy, or a combination thereof.

Aspect 66. The method of any of aspects 55-65, wherein the second flexible polymer is applied by spin coating.

Aspect 67. The method of any of aspects 55-66, wherein the second flexible polymer is porous.

Aspect 68. The method of any of aspects 55-67, wherein the second metal comprises gold, titanium, platinum, nickel, chromium, copper, silver, or a combination thereof.

Aspect 69. The method of any of aspects 55-68, wherein the second metal is deposited with a thickness of from about 30 to about 200 nm.

Aspect 70. The method of any of aspects 55-69, wherein the second photoresist is removed using a solvent.

Aspect 71. The method of aspect 70, wherein the solvent comprises acetone.

Aspect 72. The method of any of aspects 55-71, wherein the third flexible polymer comprises polydimethylsiloxane (PDMS), porous PDMS, polymethylmethacrylate (PMMA), polyimide (PI), polyurethane (PU), epoxy, or a combination thereof.

Aspect 73. The method of any of aspects 55-72, wherein the third flexible polymer is applied by spin coating.

Aspect 74. A pseudo-palate comprising an electrode array manufactured using the method of any of aspects 34-54 or the dual electrode array manufactured using the method of any of aspects 55-73.

Aspect 75. A method for diagnosing a neurological condition in a subject, the method comprising:
(a) fitting the subject with the pseudo-palate of any of aspects 1-33 or 74;
(b) requiring the subject to perform at least one vocal task;
(c) collecting acoustic data and data from the pseudo-palate generated by the performance of the at least one vocal task;
(d) comparing the acoustic data and data from the pseudo-palate to a data set from healthy subjects and subjects having diagnosed neurological conditions performing the same at least one vocal task; and
(e) diagnosing the neurological condition.

Aspect 76. The method of aspect 75, wherein the neurological condition comprises a traumatic brain injury, Parkinson's disease, dyspraxia, dysarthria, congenital sensory neuropathy, schizophrenia, depression, fatigue, stress, or a combination thereof.

Aspect 77. The method of aspect 76, wherein the traumatic brain injury comprises a concussion.

Aspect 78. The method of any of aspects 75-77, wherein the vocal task comprises a single task.

Aspect 79. The method of any of aspects 75-77, wherein the vocal task comprises a dual task.

Aspect 80. The method of aspect 78 or 79, wherein the vocal task comprises picture description, story-telling, or syllable repetition.

Aspect 81. The method of aspect 79 or 80, wherein the dual task comprises an exercise task.

Aspect 82. The method of aspect 81, wherein the exercise task comprises walking on a treadmill or pedaling a stationary bicycle.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for.

Example 1: Development of a Data-Driven Speech Stimulus Set

One component of using speech as a biomarker is the selection of speech items to test participants with. Currently, the speech tests used in concussion detection models select specific syllables, words and phrases (e.g. "pa-ta-ka" in a diadochokinetic test) without fine justifications. Furthermore, the dimensions of speech parameters extracted are typically done in an exploratory way. In this project, a data-driven approach is taken to the design of the speech stimulus set by identifying which relevant speech parameters in motor control disorders would be useful for identifying impaired articulation and by designing test items that maximize their predictive power. Large speech corpora of patients with Parkinson's disease (PD) are used here since their speech shares similar biomarkers with that of concussion patients. The corpora include speech samples from 44 idiopathic PD patients and 22 heathy older adults (HOAs) that were elicited in a picture-description task, a story-telling task and a syllable (/pa/) repetition task. All samples were collected while the subjects sat in a quiet room (a single task) and while they simultaneously cycled on a stationary bike (a dual task). PD patients also completed the tasks before and after an aerobic exercise intervention.

PD is a neurodegenerative disorder associated with deterioration of the substantia nigra pars *compacta* neurons within the basal ganglia, resulting in severe depletion of dopamine production. The low level of dopamine leads to dysfunctions of the basal ganglia and frontal lobes, adversely affecting tasks requiring fine control of muscles. These deficits negatively affect respiration, phonation, and articulation, which are controlled by the speech motor control system.

This portion of our research focuses on speech signal analysis to assess the motor speech characteristics associated with neurological disease diagnosis and traumatic brain injuries as reflected in changes in phonation, resonance, and articulation.

To develop a data-driven speech stimulus set, a two-step approach can be devised that aims a) to narrow the initial search space and b) to identify relevant and interpretable speech parameters. Step 1: Since the number of speech parameters is large, our first step is to discover which broad articulatory dimensions are particularly important for distinguishing PD patients and HOAs, thus allowing us to narrow the search space of the relevant speech parameters in motor control disorders. This is done by training a deep-learning computational model to learn the patterns of a set of broad articulatory features using a speech corpus from control subjects, and then using the model's prediction of these articulatory features to estimate the degree of speech errors contained in the speech signal of PD patients and HOAs. Based on an iterative model evaluation process, different model architectures, e.g., recurrent neural network, and the precise model parameters, such as the number of layers and neurons, will be investigated. The input speech corpus will undergo different stages of processing. The speech corpus is time-aligned with speech segment-level timestamps. Each speech segment in the speech corpus is parameterized in a representation such as Linear Predictive Codes (LPC), Perceptual Linear Prediction (PLP), Mel Frequency Cepstral Coefficients (MFCC) and other specific speech parameters. Each segment will be coded for its articulatory properties. Deep-learning models are then trained to predict the articulatory properties from the parameterized representations. The weights of the model's speech parameters are learned through training and testing over the speech corpus, for instance cross-validation. When a number of relevant broad articulatory dimensions (e.g. phonation) have been identified, the second step will be to conduct fine-grained analyses of the corresponding speech parameters using more controlled speech samples.

Example 2: Evaluation of the SELMA System with Behavioral Methods

In addition to comparing the mechanical and electrical functionality of the SELMA system including the disclosed pseudo-palate with computational modelling, the SELMA system can be evaluated against a commercial pseudo-palate by conducting behavioral experiments. Approximately 50 participants will be recruited to undergo our data-driven speech task as well as syllable elicitation tasks using both the SELMA system and a commercial counterpart. We will evaluate the level of a) between-speaker comparability and b) informativity of the EPG signals for sound recognition with and without the acoustic signals. High between-speaker comparability is desirable because it would allow us to better identify the articulatory differences due to speech pathological issues and not due to between-speaker variability. The EPG signals for each type of speech sound will be compared across speakers, for instance, using clustering analyses. To evaluate how informative the EPG signals are, we would train a speech sound recognizer using the EPG signals from both the SELMA system and the commercial device with and without the acoustic signals. This will allow us to evaluate the quality of the information the two EPGs provide beyond the information that is already in the acoustic signals.

Example 3: Deep-Learning Estimation of Speech Errors of Broad Articulatory Dimensions Interpretability of pathological speech analyses is important for clinicians for the purpose of administering assessments and designing interventions. However, studies that aim to design a classification tool for distinguishing pathological and typical speech often lack interpretability due to the type of features and the domains they compute these features over. In automatic analyses of pathological speech using machine learning, high-dimensional complex features such as Mel-Frequency Cepstrum Coefficients are often used over more basic acoustic features which are more interpretable, such as fundamental frequency, jitter, and formant frequencies.

Recent approaches have begun to bridge this gap by employing deep-learning computational models to learn phonological features which are not only interpretable but are also motivated by linguistic theories of speech production and processing. Each phonological feature is related to specific movements of articulators and is therefore suitable for understanding what aspects of the speech are particularly problematic for speakers with pathological speech patterns. Prior studies have shown that the phonological features learned from deep-learning models can be used to detect subtle production differences in pathological speech such as dysarthric speech and apraxia.

To examine if the phonological features obtained from deep-learning models are sensitive to differences between a patient with PD and a normal subject's articulation, we trained a deep-learning model using a large corpus of 360 hours of American English speech to learn 20 phonological features. The architecture of the model is a bidirectional recurrent neural network with gated recurrent units. The speech corpus was divided into an 80:20 split to form the training and the testing data respectively. The corpus was automatically annotated with timestamps of each phone and therefore each phonological class. The speech signal was segmented into 10 ms long speech frames. Using the timestamps of each phone and the segmented speech frames, the model was trained to predict whether each frame belongs to one or more phonological classes.

Figure 10:
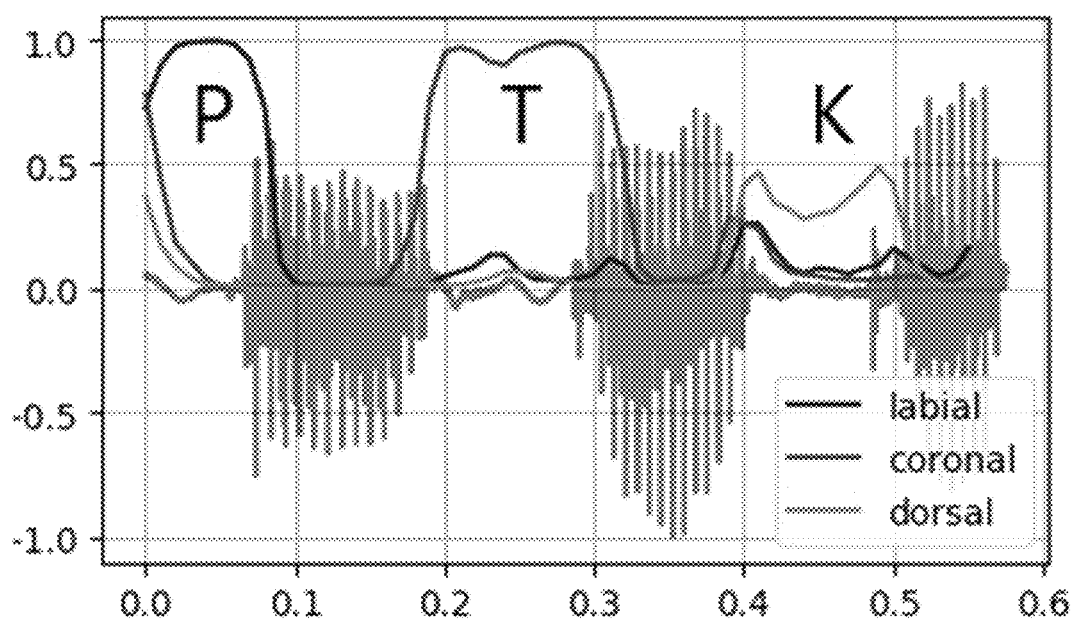
FIG. 10 shows an example of the posterior probability of labial, coronal, and dorsal articulation of consonants given the signal of the syllables "PA," "TA," and "KA," in this order. The place of articulation of P, T, and K aligns with their posterior probabilities.

The evaluation dataset is the set of story-telling task speech samples from 12 PD patients and 12 healthy older adults (HOAs) produced while sitting in a quiet room pre-intervention. The samples were automatically annotated with timestamps of each phone and segmented into speech frames. Using the deep-learning model, we computed the posterior probability of each speech frame for each phonological class (see FIG. 10). We hypothesized that pathological speech from PD patients would contain speech frames that yielded lower posterior phonological probabilities than those from HOAs. For each speech frame, a deviation score was computed for each phonological class. The deviation score was defined as the absolute difference between the posterior phonological probability and the expected probability. The deviation score reflects the degree of production errors. For instance, a speech frame from an expected 'b' sound would have an expected voicing probability of 1 because 'b' involves vocal fold vibrations, but the produced sound deviated from a typical 'b' in terms of its amount of voicing, thus it would have a lower voicing probability of 0.4, therefore the deviation score of voicing would be 0.6. The trained deep learning model generates probabilistic predictions based on the input signal. An expected probability for the predictions the model makes are generated based on knowledge of the target speech content (e.g., types of segments) and should be close to 1. If the acoustic signal deviates from the expectation, the probability will be less than 1, with the deviation score being the difference between observed and expected values.

A random forest classification method was used to classify if each speech frame belongs to a PD patient or an HOA using the phonological deviation scores as predictors. Each model consists of 100 conditional inference trees, with three randomly sampled predictors selected at each branching node. The importance of each predictor is defined as the decrease in accuracy when its values are permuted. Two models were created, one for consonant speech frames (N=104,000) and one for vowel speech frames (N=85,000). Only the deviation scores of phonological classes related to consonants were included in the consonant model, and similarly, only those scores related to vowels were included in the vowel model. All the deviation scores for both vowels and consonants were found to be important above chance. This confirms our hypothesis that the pathological speech from PD patients deviates from HOAs. Looking more closely at those features that are particularly important, the consonant model suggests the importance of two place of articulation features (labial and dorsal) and a manner feature, continuant; and the vowel model suggests the importance of the rhotic feature and the back feature. The two place features suggest that PD patients cannot accurately use their lips and tongue body to create constrictions at the correct place of articulation. The continuant feature refers to the distinction between plosives (with a complete closure, e.g. 'p' and 't') from non-plosives (without a complete closure, e.g., 'f' and 's'). Therefore, the result suggests that the PD patients cannot accurately control the degree of constrictions, producing plosives as non-plosives and vice-versa. The rhotic feature involves the tongue tip or blade being curled backward, while the back feature involves the tongue retracting towards the back of the vocal tract. Both features suggest the difficulties with fine motor controls with the tongue muscles.

These findings, particularly with the continuant feature and the place feature, suggest that a smart pseudo-palate could detect relevant speech parameters for discriminating between impaired and unimpaired speech. Recall that the pseudo-palate can capture the position, size, pressure and duration of tongue contacts with the palate. For instance, the continuant feature suggests that PD patients have difficulty creating a tight constriction, thus allowing air to flow rather than being obstructed, as it is in plosives. This could be reflected in a smaller area of tongue-palate contact that has weaker pressure when measured by the pseudo-palate.

Example 4: Fine-Grained Phonetic Analyses of Changes in Phonation

In addition to imprecise consonant and vowel articulation, 89% of PD patients develop problems in their breathing and swallowing processes, affecting several aspects in speech including phonation, articulation, and prosody and 70-90% of patients with PD show some form of vocal impairment. Phonation is the process by which airflow from the lungs passes through the vocal folds to produce sounds. Vocal fold configuration plays an important role in determining phonation types. For instance, modal or normal voice phonation is produced by the optimal combination of airflow and vocal fold tension, to produce maximum vibration; breathy voice with vibrating vocal folds while they are apart causing lung air to become turbulent and noisy as it continuously flows through the glottis or the opening between the vocal folds, and creaky voice with the posterior portion of the vocal folds held tightly together while the anterior portion is slack and vibrating at a slow rate.

Differences in amplitudes of the first and second harmonics (H1, H2) and the strongest harmonic amplitudes located at the first, second, and third formant frequency (A1, A2, A3) regions of the voice spectrum are useful for quantification of degree of glottal adduction and have been employed for analysis of normal phonation with different degrees of breathiness or to assess gender differences. Harmonic amplitude differences have also been shown to be clinically useful in characterizing breathiness in individuals with unilateral vocal fold paralysis and vocal nodules. More recently, amplitude differences have been shown to successfully differentiate pre- and post-treatment adductor spasmodic dysphonic speech (ADSD) and between ADSD and normal speech after treatment. Due to abnormal and involuntary contraction of the vocal folds, ADSD is produced with hyperadduction of the vocal folds (shorter open quotient and abrupt glottal closure); therefore, speech in ADSD has been characterized as pressed, tense, squeeze, strained-strangled and laryngealized, and exhibiting low H1 amplitude compared to amplitudes of higher harmonics.

Figure 11A:
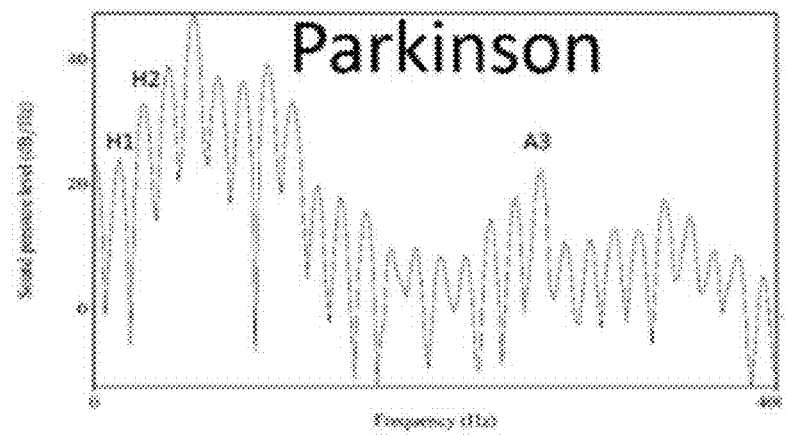
FIG. 11A shows Fast Fourier Transforms (FFT) of acoustic data of speech from a Parkinson's disease patient from the vowel portion of 10 repetitions of the/pa/syllable.
Figure 11B:
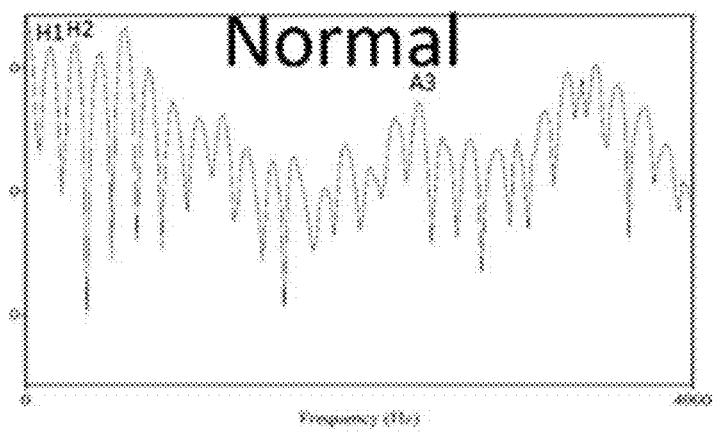
FIG. 11B shows the same for a healthy adult control.

To examine if degree of glottal adduction is sensitive to differences between a patient with PD and a normal subject's phonation, we obtained amplitude difference between H1 and H2 (H1-H2) and H1 and A3 (H1-A3) from the vowel portion of the first 10 repetitions of the /pa/ syllable produced by a male PD and a male normal control subject from both the single and the dual tasks. For PD patients only, measurements were obtained from both before and after an exercise intervention conditions. FIG. 11 shows Fast Fourier Transforms (FFT) of audio data illustrating harmonics from the center of the vowel /a/ in a repetition of the syllable /pa/ produced by the PD and the normal subject. As shown here, H1 vs H2 amplitude differences as well as H1 vs A3 differences are greater in the PD patient than in the normal subject.

PD and Normal Subject Comparison

Figure 12:
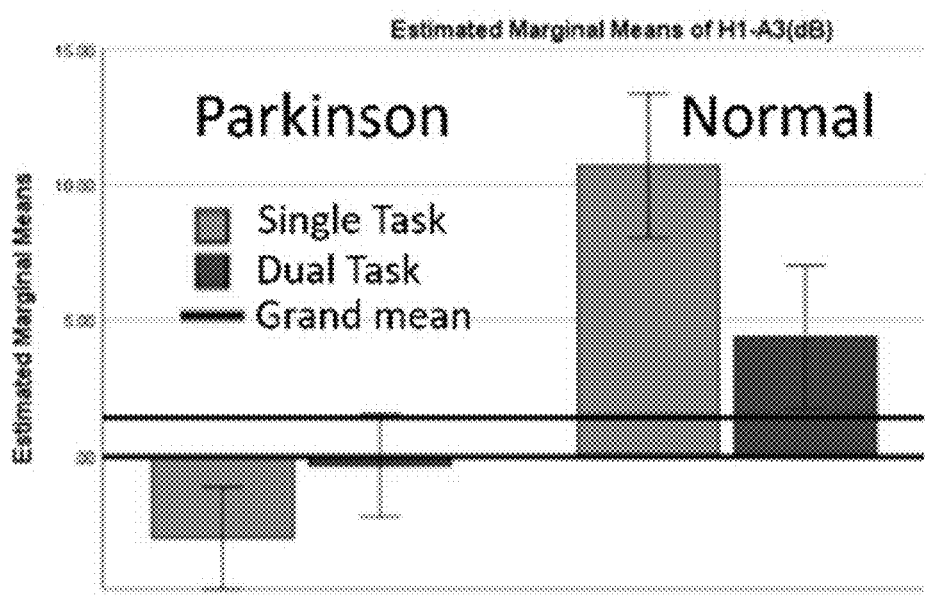
FIG. 12 shows a comparison of voice quality for Parkinson's disease patients and normal subjects performing the same speaking task as assessed using the pseudo-palate disclosed herein.

To directly compare PD patients to the normal subject, a multivariate ANOVA was performed with Task (single, dual) and Speaker (PD, NC) as fixed factors and H1-H2 and H1-A3 as dependent variables. The analysis yielded a significant main effect of Task for H1-H2 [$F(1, 56)=23.49$, $p<0.001$] but not for the H1-A3 [$F(1, 56)=2.56$, $p=0.11$]. More interestingly, a significant main effects of Speaker was found for both H1-H2 [$F(1, 56)=258.80$, $p<0.001$], with the H1 being much lower in amplitude than H2 for the PD patient than for the normal subject, and H1-A3 [$F(1, 56)=64.66$, $p<0.01$], with A3 amplitude being weaker than H1 for the PD patient, but the opposite was true for the normal patient. A significant interaction between Speaker and Task for H1-A3 [$F(1, 56)=15.41$, $p<0.001$], but not for H1-H2 [$F(1, 56)=0.55$, $p=0.46$] was also found. Follow-up tests examining the effects of Speaker for each task revealed a significant main effect of Speaker for the single task, [$F(1,28)=65.80$, $p<0.001$], with A3 being weaker than H1 for the PD patient (−2.98 dB), but the opposite was true for the normal subject (10.69 dB) (FIG. 12). A significant but less strong effect of Speaker was also found for the dual task [$F(1, 28)=0.929$, $p<0.005$]. In this case, H1 amplitude was weaker than A3 amplitude for the PD patient (−0.32 dB), but the opposite was true for the normal subject (4.38 dB) (FIG. 12).

Follow-up tests comparing the two tasks for each speaker on H1-A3 were also performed. For the PD patient, the difference between the two tasks nearly reached significance [$F(1,38)=3.30$, $p=0.077$], with A3 became relatively stronger against H1 in the dual task (H1-A3=−0.32 dB) than in the single task (H1-A3=−2.98 dB). That is, both H1 and A3 became stronger in the dual task condition than in the single task condition, but the gain was greater for A3 than for H1. For the normal subject, the difference between H1-A3 between the two tasks was highly significant [$F(1, 18)=22.02$, $p<0.001$]. However, unlike the PD patient, H1 became relative weaker against A3 in the dual task (4.38 dB) compared to the single task (10.69 dB).

In sum, our preliminary data suggested that degeneration of the neuromotor system resulted in the inability to precisely control articulators, which impaired tongue and lip movements during consonant and vowel production and also affected the degree of glottal adduction during phonation. These data will inform our stimulus design and the design specification of the proposed SELMA system such that it can provide articulatory information about the location, size, pressure and duration of tongue contact that is complementary to acoustic information for linguistic and medical purposes.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Asaei, A., et al. (2016). PAoS markers: Trajectory analysis of selective phonological posteriors for assessment of progressive apraxia of speech. In Proceeding on the 7th Workshop on Speech and Language Processing for Assistive Technologies (pp. 50-55). SLPAT.
2. Baldoli, I., et al. (2017, July). A pressure-sensitive palatograph for speech analysis. In 2017 39th Annual International Conference of the IEEE Engineering in Medicine and Biology Society (EMBC) (pp. 4431-4434). IEEE.
3. Bombien, L. et al. (2010). Prosodic and segmental effects on EPG contact patterns of word-initial German clusters. Journal of Phonetics, 38(3), 388-403.
4. Borghetti, M. et al. (2016). Measuring inside your mouth! Measurement approaches, design considerations, and one example for tongue pressure monitoring. IEEE Instrumentation & Measurement Magazine, 19(5), 41-48.
5. Byrd, D. et al. (1996). Saying consonant clusters quickly. Journal of Phonetics, 24(2), 263-282.
6. Cannito, M. P. et al. (1981). Spastic dysphonia: a continuum disorder. Journal of communication disorders, 14(3), 215-223.
7. Cannito, M. P., et al. (2005). Spectral amplitude measures of adductor spasmodic dysphonic speech. Journal of Voice, 19(3), 391-410.
8. Cernak, M. et al. (2016) "Phonvoc: A phonetic and phonological vocoding toolkit," in Proceedings of INTERSPEECH 2016, pp. 988-992.
9. Cernak, M., et al. (2017). Characterisation of voice quality of Parkinson's disease using differential phonological posterior features. Computer Speech & Language, 46, 196-208.
10. Cheng, X. (2013). Wireless Biomedical Telemetry Systems Based on Flexible Metamaterial Circuits and Advanced Rf Architectures (Doctoral dissertation, University of Florida).
11. Cho, T. (2001). Effects of morpheme boundaries on intergestural timing: Evidence from Korean. Phonetica, 58(3), 129-162.
12. Correll, J. (2015). Multifunctional Smart Mouthguard Platform for Health Monitoring and Intervention for the Internet of Things (Honors Thesis, University of Florida).
13. Correll, J., et al. (2015) "Intelligent Mouthguard for Fitness and Sports," in Global Youth Innovation Festival 2015.
14. Correll, J., et al. (2015) "Multifunctional Smart Mouthguard for Health Monitoring and Intervention," in 2015 International Contest of Applications in Nano-/Micro Technologies (iCAN'15), 2015 (Silver prize winner).
15. Crawford, R. (1995). Teaching voiced velar stops to profoundly deaf children, using EPG-two case studies. Clinical linguistics & phonetics, 9(3), 255-269.
16. Fabus, R., et al. (2015). Preliminary case studies investigating the use of electropalatography (EPG) manufactured by Completespeech® as a biofeedback tool in intervention. International Journal of Linguistics and Communication, 3(1), 11-23.
17. Fletcher, S. G., et al. (1978). "Pseudo Palate useful for diagnosis and treatment of speech impairment". U.S. Pat. No. 4,112,596. Washington, DC: U.S. Patent and Trademark Office.
18. Forno, L. S. (1988). The neuropathology of Parkinson's disease. In Progress in Parkinson Research (pp. 11-21). Springer, Boston, MA.
19. Fujiwara, Y. (2007). Electropalatography home training using a portable training unit for Japanese children with cleft palate. Advances in Speech Language Pathology, 9(1), 65-72.
20. Gupta, R., et al. (2016). Pathological speech processing: State-of-the-art, current challenges, and future directions. In 2016 IEEE International Conference on Acoustics, Speech and Signal Processing (ICASSP) (pp. 6470-6474). IEEE.
21. Hamilton, C. (1993). Investigation of the articulatory patterns of young adults with Down's syndrome using electropalatography. DOWNS SYNDROME RESEARCH AND PRACTICE, 1, 15-28.
22. Hamlet, S. L. et al. (1986). Articulatory asymmetries. The Journal of the Acoustical Society of America, 79(4), 1164-1169.
23. Hanson, H. M. (1997). Glottal characteristics of female speakers: Acoustic correlates. The Journal of the Acoustical Society of America, 101(1), 466-481.
24. Hanson, H. M., et al. (1999). Glottal characteristics of male speakers: Acoustic correlates and comparison with female data. The Journal of the Acoustical Society of America, 106(2), 1064-1077.
25. Hanson, H. M., et al. (2001). Towards models of phonation. Journal of Phonetics, 29(4), 451-480.
26. Hardcastle, W. J. et al. (1997). Electropalatography and its clinical applications. Instrumental clinical phonetics, 149-193.
27. Hardcastle, W. J., et al. (1991). Visual display of tongue-palate contact: electropalatography in the assessment and remediation of speech disorders. International Journal of Language & Communication Disorders, 26(1), 41-74.
28. Hartl, D. M., et al. (2001). Objective voice quality analysis before and after onset of unilateral vocal fold paralysis. Journal of Voice, 15(3), 351-361.
29. Hlavnička, J., et al. (2017). Automated analysis of connected speech reveals early biomarkers of Parkinson's disease in patients with rapid eye movement sleep behaviour disorder. Scientific reports, 7(1), 1-13.
30. Ho, A. K., et al. (1999). Speech impairment in a large sample of patients with Parkinson's disease. Behavioural neurology, 11(3), 131-137.
31. Howell, J., et al. (2017). Acoustic classification of focus: On the web and in the lab. Laboratory Phonology: Journal of the Association for Laboratory Phonology, 8(1), 16. DOI: http://doi.org/10.5334/labphon.8
32. Izdebski, K. (1992). Symptomatology of adductor spasmodic dysphonia: a physiologic model. Journal of Voice, 6(4), 306-319.
33. Jiao, Y., et al. (2017). Interpretable phonological features for clinical applications. In 2017 IEEE international conference on acoustics, speech and signal processing (ICASSP) (pp. 5045-5049). IEEE.
34. Kraus, N., et al. (2016). Auditory biological marker of concussion in children. Scientific reports, 6, 39009.
35. Krynicki, G., et al. (2019). Automatic English phoneme recognition from articulatory data generated by EPG systems with grid and anatomical layout of contact sensors. In Proceedings of the 19th International Congress of Phonetic Sciences, Melbourne, Australia 2019 (pp. 492-496)
36. Logemann, J. A. et al. (1978). Frequency and cooccurrence of vocal tract dysfunctions in the speech of a large sample of Parkinson patients. Journal of Speech and hearing Disorders, 43(1), 47-57.
37. McAuliffe, M. et al. (2017). Montreal Forced Aligner: Trainable Text-Speech Alignment Using Kaldi. In Interspeech (pp. 498-502).
38. Miyawaki, K. (1972). A preliminary study of American English/r/by use of dynamic palatography. Ann. Bull. Res. Inst. Logop. Phoniatr., Univ. Tokyo, 8, 51-57.
39. Panayotov, V. et al. (2015, April). Librispeech: an ASR corpus based on public domain audio books. In 2015 IEEE International Conference on Acoustics, Speech and Signal Processing (ICASSP) (pp. 5206-5210). IEEE.
40. Poellabauer, C. et al. (2015). Challenges in concussion detection using vocal acoustic biomarkers. IEEE Access, 3, 1143-1160.
41. Poellabauer, C. et al. (2016) University of Notre Dame. Systems and methods for using isolated vowel sounds for assessment of mild traumatic brain injury. U.S. patent application Ser. No. 15/005,703.
42. Rosenbek, J. C. et al. (2018), University of Florida Research Foundation Inc and Michigan State University. Screening for neurological disease using speech articulation characteristics. U.S. Pat. No. 10,010,288.
43. Ruiz, L. M. (2018). Propuesta de electropalatógrafo. Una solución anatómica universal e inalámbrica.
44. Rusz, J. et al. (2011). Quantitative acoustic measurements for characterization of speech and voice disorders in early untreated Parkinson's disease. The journal of the Acoustical Society of America, 129(1), 350-367.
45. Sardini, E. et al. (2013, June). Wireless intraoral sensor for the physiological monitoring of tongue pressure. In 2013 Transducers & Eurosensors XXVII: The 17th International Conference on Solid-State Sensors, Actuators and Microsystems (TRANSDUCERS & EUROSENSORS XXVII) (pp. 1282-1285). IEEE.
46. Sardini, E. et al. (2014, June). Analysis of tongue pressure sensor for biomedical applications. In 2014 IEEE International Symposium on Medical Measurements and Applications (MeMeA) (pp. 1-5). IEEE.
47. Shibata, S., et al. (1978). A new portable type unit for electropalatography. Annual Bulletin of Research Institute of Logopedics and Phoniatrics, 12, 5-10.
48. Skodda, S., et al. (2011). Vowel articulation in Parkinson's disease. Journal of voice, 25(4), 467-472.
49. Tiede, M., et al. (2003). A new approach to pressure-sensitive palatography using a capacitive sensing device. In Proceedings of the 15th International Congress of Phonetic Sciences, Barcelona (pp. 3149-3152).
50. Timmins, C. et al. (2011). An EPG analysis of/t/in young people with Down's syndrome. Clinical linguistics & phonetics, 25(11-12), 1022-1027.
51. US 2016/0135732 A1: SYSTEMS AND METHODS FOR USING ISOLATED VOWEL SOUNDS FOR ASSESSMENT OF MILD TRAUMATIC BRAIN INJURY (May 19, 2016)
52. U.S. Pat. No. 9,579,056 B2: SCREENING FOR NEUROLOGICAL DISEASE USING SPEECH ARTICULATION CHARACTERISTICS (Feb. 28, 2017)
53. Vásquez-Correa, J. C., et al. (2019). Phonet: a Tool Based on Gated Recurrent Neural Networks to Extract Phonological Posteriors from Speech. Proc. Interspeech 2019, 549-553.
54. Wakumoto, M. et al. (1998). A pressure sensitive palatography: Application of new pressure sensitive sheet for measuring tongue-palatal contact pressure. In Fifth International Conference on Spoken Language Processing.
55. Wrench, A. A. (2007). Advances in EPG palate design. Advances in Speech Language Pathology, 9(1), 3-12.
56. Zhao, Y. et al. (2009). Three dimensional metal pattern transfer for replica molded microstructures. Applied Physics Letters, 94(2), 10.

What is claimed is:

1. A pseudo-palate comprising:
a flexible material comprising an anterior end and a posterior end;
a plurality of detecting electrodes embedded in the flexible material, each having a diameter from about 100 µm to about 1 mm in diameter and a thickness of about 200 nm;
a plurality of tracing lines having a width of from about 5 µm to about 50 µm embedded in the flexible material and each connected to a respective electrode of the plurality of electrodes, wherein the tracing lines comprises a width of from about 5 µm to about 50 µm;
a wireless microprocessor module adapted to be positioned along an outer wall of a first posterior portion of the subject's upper gums;
a battery adapted to be positioned along an outer wall of a second posterior portion of the subject's upper gums;
a first wire electrically connected to the plurality of tracing lines and extending from the posterior end of the flexible material and adapted to surround a first posterior-lateral corner of the subject's upper gum to electrically connect to the wireless microprocessor module; and
a second wire electrically connected to the plurality of tracing lines and extending from the posterior end of the flexible material and adapted to surround a second posterior-lateral corner of the subject's upper gum to electrically connect to the battery;
wherein the pseudo-palate is from about 0.1 mm to about 0.2 mm thick, and wherein the plurality of electrodes are configured for resistive sensing of tongue contact with a subject's hard palate.

2. The pseudo-palate of claim 1, wherein the electrodes comprise gold, titanium, platinum, chromium, nickel, copper, silver, or a combination thereof.

3. The pseudo-palate of claim 1, wherein the pseudo-palate comprises from 64 to 4096 electrodes.

4. The pseudo-palate of claim 1, wherein the tracing lines comprise gold, titanium, platinum, nickel, copper, silver, or a combination thereof.

5. The pseudo-palate of claim 1, wherein the flexible material comprises polydimethylsiloxane (PDMS), porous PDMS, polymethylmethacrylate (PMMA), polyimide (PI), polyurethane (PU), epoxy, or a combination thereof.

6. The pseudo-palate of claim 1, further comprising a mouth guard, a pressure sensor, a temperature sensor, an inertia sensor, an accelerometer, a gyroscope, a magnetometer, an infrared sensor for monitoring impacts, a heart rate monitor, or any combination thereof.

7. The pseudo-palate of claim 1, wherein the pseudo-palate is disposable.

8. A pseudo-palate comprising:
a flexible material comprising an anterior end and a posterior end;
a top array comprising a plurality of rows of electrodes and a bottom array comprising a plurality of columns of electrodes embedded in the flexible material, wherein the top array is disposed over the bottom array and are separated by a gap such that when the pseudo-palate is worn by a subject, the top array is close to a subject's hard palate than the bottom array and the gap is adapted to decrease when a tongue contacts the subject's hard palate, a first straight-line interconnects, each configured to electrically connect electrodes along a respective row of the plurality of rows of electrodes;

a second straight-line interconnects, each configured to electrically connect electrodes along a respective column of the plurality of columns of electrodes;

wherein each electrode of the plurality of row of electrodes and the plurality of column electrodes has a diameter from 100 μm to 1 mm in diameter and a thickness of about 200 nm;

a wireless microprocessor module adapted to be positioned along an outer wall of a first posterior portion of the subject's upper gums;

a battery adapted to be positioned along an outer wall of a second posterior portion of the subject's upper gums;

a first wire electrically connected to the first and second straight-line interconnects extending from the posterior end of the flexible material and adapted to surround a first posterior-lateral corner of the subject's upper gum to electrically connect to the wireless microprocessor module; and a second wire electrically connected to the first and second straight-line interconnects of the flexible material extending from the posterior end of the flexible material and adapted to surround a second posterior-lateral corner of the subject's upper gum to electrically connect to the battery;

wherein the pseudo-palate is from 60 μm to 200 μm thick; and wherein the plurality of electrodes are configured for capacitive sensing of tongue contact with the subject's hard palate.

9. The pseudo-palate of claim 8, wherein the top array of electrodes and the bottom array of electrodes comprise gold, titanium, platinum, nickel, chromium, copper, silver, or a combination thereof.

10. The pseudo-palate of claim 8, wherein the flexible material comprises polydimethylsiloxane (PDMS), porous PDMS, polymethylmethacrylate (PMMA), polyimide (PI), polyurethane (PU), epoxy, or a combination thereof.

11. The pseudo palate of claim 8, further comprising a pressure sensor, a temperature sensor, an inertia sensor, an accelerometer, a gyroscope, a magnetometer, an infrared sensor for monitoring impacts, a heart rate monitor, or a combination thereof.

12. The pseudo palate of claim 8, wherein the pseudo-palate is disposable.

13. A method for diagnosing a neurological condition in a subject, the method comprising:
    (a) fitting the subject with the pseudo-palate of claim 8;
    (b) requiring the subject to perform at least one vocal task;
    (c) collecting acoustic data and data from the pseudo-palate generated by the performance of the at least one vocal task;
    (d) comparing the acoustic data and data from the pseudo-palate to a data set from healthy subjects and subjects having diagnosed neurological conditions performing the same at least one vocal task; and
    (e) diagnosing the neurological condition.

14. The method of claim 13, wherein the neurological condition comprises a traumatic brain injury, Parkinson's disease, dyspraxia, dysarthria, congenital sensory neuropathy, schizophrenia, depression, fatigue, stress, or a combination thereof.

15. The pseudo palate of claim 1, wherein the gap comprises a polydimethylsiloxane insulator layer.

* * * * *